(12) United States Patent
Jensen et al.

(10) Patent No.: US 7,935,501 B2
(45) Date of Patent: May 3, 2011

(54) RECOMBINANT PRODUCTION OF ANTIMICROBIAL PEPTIDES

(75) Inventors: Ejner Bech Jensen, Virum (DK); Hans-Henrik Kristensen Høgenhaug, Holte (DK); Peter Kamp Hansen, Lejre (DK); Poul Erik Pedersen, Soborg (DK); Per Holse Mygind, Soborg (DK)

(73) Assignee: Novozymes Pharma Biotec A/S, Bagsvaerd (DK)

( * ) Notice: Subject to any disclaimer, the term of this patent is extended or adjusted under 35 U.S.C. 154(b) by 0 days.

(21) Appl. No.: 10/572,016

(22) PCT Filed: Sep. 13, 2004

(86) PCT No.: PCT/DK2004/000605
§ 371 (c)(1), (2), (4) Date: Mar. 20, 2006

(87) PCT Pub. No.: WO2005/024002
PCT Pub. Date: Mar. 17, 2005

(65) Prior Publication Data
US 2007/0104764 A1    May 10, 2007

Related U.S. Application Data

(60) Provisional application No. 60/502,761, filed on Sep. 12, 2003.

(30) Foreign Application Priority Data

Sep. 11, 2003 (DK) .................................. 2003 01310

(51) Int. Cl.
*C12N 1/21* (2006.01)
*C07K 14/195* (2006.01)
*A23K 1/165* (2006.01)

(52) U.S. Cl. ... 435/69.1; 435/69.7; 435/325; 435/320.1; 435/410; 435/252.3; 530/300; 530/350; 424/442

(58) Field of Classification Search ................. 435/325, 435/320.1, 410, 252.3, 69.1, 69.7; 424/442; 530/350, 300
See application file for complete search history.

(56) References Cited

FOREIGN PATENT DOCUMENTS

| WO | WO 96/14413 | 5/1996 |
|---|---|---|
| WO | WO 96/28559 | 9/1996 |
| WO | WO 98/54336 | 12/1998 |
| WO | WO 00/75344 | 12/2000 |

OTHER PUBLICATIONS

The American heritage Distionary, second college addition, p. 174, 919-920 (1982).*
Okamoto et al., Plant Cell Physiol, vol. 39, No. 1, pp. 57-63 (1998).
Morreale et al., Journal of Chromatography B, vol. 786, pp. 237-246 (2003).
Shi et al., Antimicrobial Agents and Chemotherapy, vol. 40, No. 1, pp. 115-121 (1996).
Sarmaslk et al., Marine Biotechnology, vol. 4, pp. 310-322 (2002).
Graczynska et al., Biochemistry, vol. 42, pp. 8663-8670 (2003).

* cited by examiner

*Primary Examiner* — Chih-Min Kam
(74) *Attorney, Agent, or Firm* — Elias Lambiris

(57) ABSTRACT

The invention relates to the use of co-expression of an antimicrobial agent and an enzyme, with a view to improving yield and/or overall production economy. Examples of antimicrobial agents are antimicrobial peptides such as lactoferricins and antimicrobial enzymes such as lysozyme and glucose oxidase, and examples of enzymes are endoglucanase, xylanase, phytase, protease, galactanase, mannanase, dextranase, alpha-galactosidase, pectate lyase, alpha-amylase and glucoamylase. A fusion product comprising the antimicrobial agent and the enzyme and a cleavable linker is novel, and can be used in animal feed and animal feed additives. The invention also describes the use of a protection domain wherein at least 50% of the amino acid residues comprised in the peptide protection domain are D (Asp) and/or E (Glu). The protection or quenching domain serves to temporarily and reversibly inactivate the antimicrobial peptide during the expression.

25 Claims, No Drawings ically, a synthetic IgG-binding domains (ZZ) of protein A, and outer membrane protein F from *Pseudomonas aeruginosa*.

SEQUENCE LISTING

```
<160> NUMBER OF SEQ ID NOS: 118

<210> SEQ ID NO 1
<211> LENGTH: 20
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(20)
<220> FEATURE:
<221> NAME/KEY: DISULFID
<222> LOCATION: (2)..(19)

<400> SEQUENCE: 1

Lys Cys Arg Arg Trp Gln Trp Arg Met Lys Lys Leu Gly Ala Pro Ser
1               5                   10                  15

Ile Thr Cys Val
            20

<210> SEQ ID NO 2
<211> LENGTH: 20
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: The thiol group of the Cys in position 2 is
      blocked
<220> FEATURE:
<221> NAME/KEY: MISC_FEATURE
<223> OTHER INFORMATION: The thiol group of the Cys in position 19 is
      blocked
<220> FEATURE:
<221> NAME/KEY: PEPTIDE
<222> LOCATION: (1)..(20)

<400> SEQUENCE: 2

Lys Cys Arg Arg Trp Gln Trp Arg Met Lys Lys Leu Gly Ala Pro Ser
1               5                   10                  15

Ile Thr Cys Val
            20

<210> SEQ ID NO 3
<211> LENGTH: 20
<212> TYPE: PRT
<213> ORGANISM: Artificial Sequence
<220> FEATURE:
```

```
<223> OTHER INFORMATION: Peptide
<220> FEATURE:
<221> NAME/KEY: PEPTIDE
<222> LOCATION: (1)..(20)
<220> FEATURE:
<221> NAME/KEY: DISULFID
<222> LOCATION: (2)..(19)

<400> SEQUENCE: 3

Lys Cys Phe Gln Trp Gln Arg Asn Met Arg Lys Val Arg Gly Pro Pro
1               5                   10                  15

Val Ser Cys Ile
            20

<210> SEQ ID NO 4
<211> LENGTH: 20
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: The thiol group of Cys in position 2 is
      blocked
<220> FEATURE:
<221> NAME/KEY: MISC_FEATURE
<223> OTHER INFORMATION: The thiol group of Cys in position 19 is
      blocked
<220> FEATURE:
<221> NAME/KEY: PEPTIDE
<222> LOCATION: (1)..(20)

<400> SEQUENCE: 4

Lys Cys Phe Gln Trp Gln Arg Asn Met Arg Lys Val Arg Gly Pro Pro
1               5                   10                  15

Val Ser Cys Ile
            20

<210> SEQ ID NO 5
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 5

Arg Trp Gln Trp Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 6

Arg Arg Gln Trp Arg
1               5

<210> SEQ ID NO 7
<211> LENGTH: 5
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(5)

<400> SEQUENCE: 7

Lys Val Ser Trp Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 8

Arg Asn Met Arg Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 9

Arg Trp Gln Glu Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)

<400> SEQUENCE: 10

Arg Arg Trp Gln Trp Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)

<400> SEQUENCE: 11

Arg Arg Arg Gln Trp Arg
1               5

<210> SEQ ID NO 12
<211> LENGTH: 6
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(6)

<400> SEQUENCE: 12

Lys Thr Val Ser Trp Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)

<400> SEQUENCE: 13

Lys Arg Asn Met Arg Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)

<400> SEQUENCE: 14

Arg Trp Gln Glu Met Lys
1               5

<210> SEQ ID NO 15
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(11)

<400> SEQUENCE: 15

Lys Thr Arg Arg Trp Gln Trp Arg Met Lys Lys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(11)

<400> SEQUENCE: 16

Lys Ser Arg Arg Arg Gln Trp Arg Met Lys Lys
1               5                   10

<210> SEQ ID NO 17
<211> LENGTH: 11
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(11)

<400> SEQUENCE: 17

Lys Thr Val Ser Trp Gln Thr Tyr Met Lys Lys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(11)

<400> SEQUENCE: 18

Lys Thr Phe Gln Trp Gln Arg Asn Met Arg Lys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(11)

<400> SEQUENCE: 19

Lys Thr Leu Arg Trp Gln Asn Glu Met Arg Lys
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)

<400> SEQUENCE: 20

Phe Gln Trp Gln Arg Asn
1               5

<210> SEQ ID NO 21
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 21

Phe Gln Trp Gln Arg
1               5

<210> SEQ ID NO 22
<211> LENGTH: 4
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(4)

<400> SEQUENCE: 22

Gln Trp Gln Arg
1

<210> SEQ ID NO 23
<211> LENGTH: 3
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(3)

<400> SEQUENCE: 23

Trp Gln Arg
1

<210> SEQ ID NO 24
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 24

Arg Arg Trp Gln Trp
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(4)

<400> SEQUENCE: 25

Arg Arg Trp Gln
1

<210> SEQ ID NO 26
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(4)

<400> SEQUENCE: 26

Trp Gln Trp Arg
1

<210> SEQ ID NO 27
<211> LENGTH: 3
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(3)

<400> SEQUENCE: 27

Gln Trp Arg
1

<210> SEQ ID NO 28
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(3)

<400> SEQUENCE: 28

Leu Arg Trp Gln Asn Asp
1               5

<210> SEQ ID NO 29
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)

<400> SEQUENCE: 29

Leu Arg Trp Gln Asn
1               5

<210> SEQ ID NO 30
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(4)

<400> SEQUENCE: 30

Leu Arg Trp Gln
1

<210> SEQ ID NO 31
<211> LENGTH: 3
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(3)

<400> SEQUENCE: 31

Arg Trp Gln
1

<210> SEQ ID NO 32
<211> LENGTH: 25
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(25)

<400> SEQUENCE: 32

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 33
<211> LENGTH: 11
<212> TYPE: PRT
<213> ORGANISM: Artificial
<220> FEATURE:
<223> OTHER INFORMATION: Peptide
<220> FEATURE:
<221> NAME/KEY: PEPTIDE
<222> LOCATION: (1)..(11)
<220> FEATURE:
<221> NAME/KEY: Misc_feature
<222> LOCATION: (2)..(5)
<223> OTHER INFORMATION: Xaa denotes any amino acid
<220> FEATURE:
<221> NAME/KEY: Misc_feature
<222> LOCATION: (7)..(8)
<223> OTHER INFORMATION: Xaa denotes any amino acid

<400> SEQUENCE: 33

Lys Xaa Xaa Xaa Xaa Gln Xaa Xaa Met Lys Lys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(11)
<220> FEATURE:
<221> NAME/KEY: Misc_feature
<222> LOCATION: (2)..(5)
<223> OTHER INFORMATION: Xaa denotes any amino acid
<220> FEATURE:
<221> NAME/KEY: Misc_feature
<222> LOCATION: (7)..(8)
<223> OTHER INFORMATION: Xaa denotes any amino acid

<400> SEQUENCE: 34

Lys Xaa Xaa Xaa Xaa Gln Xaa Xaa Met Arg Lys
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)
<220> FEATURE:
<221> NAME/KEY: Misc_feature
<222> LOCATION: (2)..(5)
<223> OTHER INFORMATION: Xaa denotes any amino acid

<400> SEQUENCE: 35

Arg Xaa Xaa Xaa Xaa Arg
```

```
1               5

<210> SEQ ID NO 36
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)
<220> FEATURE:
<221> NAME/KEY: misc_feature
<222> LOCATION: (2)..(5)
<223> OTHER INFORMATION: Xaa denotes any amino acid

<400> SEQUENCE: 36

Lys Xaa Xaa Xaa Xaa Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)
<220> FEATURE:
<221> NAME/KEY: Misc_feature
<222> LOCATION: (2)..(5)
<223> OTHER INFORMATION: Xaa denotes any amino acid

<400> SEQUENCE: 37

Lys Xaa Xaa Xaa Xaa Lys
1               5

<210> SEQ ID NO 38
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)
<220> FEATURE:
<221> NAME/KEY: Misc_feature
<222> LOCATION: (2)..(5)
<223> OTHER INFORMATION: Xaa denotes any amino acid

<400> SEQUENCE: 38

Arg Xaa Xaa Xaa Xaa Lys
1               5

<210> SEQ ID NO 39
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)
<220> FEATURE:
<221> NAME/KEY: Misc_feature
<222> LOCATION: (2)..(4)
<223> OTHER INFORMATION: Xaa denotes any amino acid

<400> SEQUENCE: 39

Arg Xaa Xaa Xaa Arg
```

```
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(5)
<220> FEATURE:
<221> NAME/KEY: Misc_feature
<222> LOCATION: (2)..(4)
<223> OTHER INFORMATION: Xaa denotes any amino acid

<400> SEQUENCE: 40

Lys Xaa Xaa Xaa Arg
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(5)
<220> FEATURE:
<221> NAME/KEY: Misc_feature
<222> LOCATION: (2)..(4)
<223> OTHER INFORMATION: Xaa denotes any amino acid

<400> SEQUENCE: 41

Arg Xaa Xaa Xaa Lys
1               5

<210> SEQ ID NO 42
<211> LENGTH: 38
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(38)

<400> SEQUENCE: 42

Lys Asn Val Arg Trp Cys Thr Ile Ser Gln Pro Glu Trp Phe Lys Cys
1               5                   10                  15

Arg Arg Trp Gln Trp Arg Met Lys Lys Leu Gly Ala Pro Ser Ile Thr
            20                  25                  30

Cys Val Arg Arg Ala Phe
        35

<210> SEQ ID NO 43
<211> LENGTH: 32
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(32)

<400> SEQUENCE: 43

Thr Ile Ser Gln Pro Glu Trp Phe Lys Cys Arg Arg Trp Gln Trp Arg
1               5                   10                  15
```

```
Met Lys Lys Leu Gly Ala Pro Ser Ile Thr Cys Val Arg Arg Ala Phe
            20                  25                  30
```

```
<210> SEQ ID NO 44
<211> LENGTH: 36
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(36)

<400> SEQUENCE: 44

Val Ser Gln Pro Glu Ala Thr Lys Cys Phe Gln Trp Gln Arg Asn Met
1               5                   10                  15

Arg Lys Val Arg Gly Pro Pro Val Ser Cys Ile Lys Arg Asp Ser Pro
            20                  25                  30

Ile Gln Cys Ile
        35

<210> SEQ ID NO 45
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(5)
<220> FEATURE:
<221> NAME/KEY: Misc_feature
<222> LOCATION: (2)..(4)
<223> OTHER INFORMATION: Xaa denotes any amino acid

<400> SEQUENCE: 45

Lys Xaa Xaa Xaa Lys
1               5

<210> SEQ ID NO 46
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(11)

<400> SEQUENCE: 46

Gly Arg Arg Arg Arg Ser Val Gln Trp Cys Ala
1               5                   10

<210> SEQ ID NO 47
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(50)

<400> SEQUENCE: 47

Ala Pro Arg Lys Asn Val Arg Trp Cys Thr Ile Ser Gln Pro Glu Trp
1               5                   10                  15

Phe Lys Cys Arg Arg Trp Gln Trp Arg Met Lys Lys Leu Gly Ala Pro
            20                  25                  30
```

```
Ser Ile Thr Cys Val Arg Arg Ala Phe Ala Leu Glu Cys Ile Arg Ala
        35                  40                  45
Ile Ala
    50
```

<210> SEQ ID NO 48
<211> LENGTH: 18
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(18)

<400> SEQUENCE: 48

```
Pro Glu Trp Phe Lys Cys Arg Arg Trp Gln Trp Arg Met Lys Lys Leu
1               5                   10                  15
Gly Ala
```

<210> SEQ ID NO 49
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(15)

<400> SEQUENCE: 49

```
Phe Lys Cys Arg Arg Trp Gln Trp Arg Met Lys Lys Leu Gly Ala
1               5                   10                  15
```

<210> SEQ ID NO 50
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(14)

<400> SEQUENCE: 50

```
Lys Cys Arg Arg Trp Gln Trp Arg Met Lys Lys Leu Gly Ala
1               5                   10
```

<210> SEQ ID NO 51
<211> LENGTH: 13
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(13)

<400> SEQUENCE: 51

```
Cys Arg Arg Trp Gln Trp Arg Met Lys Lys Leu Gly Ala
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: Peptide
<220> FEATURE:

```
<221> NAME/KEY: PEPTIDE
<222> LOCATION: (1)..(12)

<400> SEQUENCE: 52

Arg Arg Trp Gln Trp Arg Met Lys Lys Leu Gly Ala
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(15)

<400> SEQUENCE: 53

Lys Lys Cys Arg Arg Trp Gln Trp Arg Met Lys Lys Leu Gly Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(15)

<400> SEQUENCE: 54

Phe Lys Cys Phe Arg Trp Gln Trp Arg Met Lys Lys Leu Gly Ala
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(15)

<400> SEQUENCE: 55

Lys Lys Cys Phe Arg Trp Gln Trp Arg Met Lys Lys Leu Gly Ala
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(14)

<400> SEQUENCE: 56

Phe Lys Cys Arg Arg Trp Gln Trp Arg Met Lys Lys Leu Gly
1               5                   10

<210> SEQ ID NO 57
<211> LENGTH: 19
<212> TYPE: PRT
<213> ORGANISM: Artificial Sequence
<220> FEATURE:
<223> OTHER INFORMATION: Peptide
<220> FEATURE:
```

```
<221> NAME/KEY: PEPTIDE
<222> LOCATION: (1)..(19)

<400> SEQUENCE: 57

Cys Arg Arg Trp Gln Trp Arg Met Lys Lys Leu Gly Ala Pro Ser Ile
1               5                   10                  15

Thr Cys Val

<210> SEQ ID NO 58
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(6)

<400> SEQUENCE: 58

Arg Arg Trp Gln Trp Arg
1               5

<210> SEQ ID NO 59
<211> LENGTH: 188
<212> TYPE: PRT
<213> ORGANISM: Nocardiopsis sp.
<220> FEATURE:
<221> NAME/KEY: mat_peptide
<222> LOCATION: (1)..(188)

<400> SEQUENCE: 59

Ala Asp Ile Ile Gly Gly Leu Ala Tyr Thr Met Gly Arg Cys Ser
1               5                   10                  15

Val Gly Phe Ala Ala Thr Asn Ala Ala Gly Gln Pro Gly Phe Val Thr
                20                  25                  30

Ala Gly His Cys Gly Arg Val Gly Thr Gln Val Thr Ile Gly Asn Gly
            35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Ala Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 60
<211> LENGTH: 354
<212> TYPE: PRT
<213> ORGANISM: Nocardiopsis dassonvillei subsp. dassonvillei
<220> FEATURE:
<221> NAME/KEY: mat_peptide
```

<222> LOCATION: (167)..(354)

<400> SEQUENCE: 60

```
Ala Pro  Ala Pro Val Pro Gln  Thr Pro Val Ala Asp  Asp Ser Ala
    -165             -160                  -155

Ala Ser  Met Thr Glu Ala Leu  Lys Arg Asp Leu Asp  Leu Thr Ser
    -150             -145                  -140

Ala Glu  Ala Glu Glu Leu Leu  Ser Ala Gln Glu Ala  Ala Ile Glu
    -135             -130                  -125

Thr Asp  Ala Glu Ala Thr Glu  Ala Ala Gly Glu Ala  Tyr Gly Gly
    -120             -115                  -110

Ser Leu  Phe Asp Thr Glu Thr  Leu Glu Leu Thr Val  Leu Val Thr Asp
    -105             -100                  -95

Ala Ser  Ala Val Glu Ala Val  Glu Ala Thr Gly Ala  Gln Ala Thr Val
    -90              -85                   -80                -75

Val Ser  His Gly Thr Glu Gly  Leu Thr Glu Val Val  Glu Asp Leu Asn
                 -70                  -65                   -60

Gly Ala  Glu Val Pro Glu Ser  Val Leu Gly Trp Tyr  Pro Asp Val Glu
             -55                  -50                   -45

Ser Asp  Thr Val Val Glu Val  Leu Glu Gly Ser Asp  Ala Asp Val
             -40                  -35                   -30

Ala Ala  Leu Leu Ala Asp Ala  Gly Val Asp Ser Ser  Val Arg Val
    -25              -20                   -15

Glu Glu  Ala Glu Glu Ala Pro  Gln Val Tyr Ala Asp  Ile Ile Gly Gly
    -10              -5                    -1   1                5

Leu Ala  Tyr Tyr Met Gly Gly  Arg Cys Ser Val Gly  Phe Ala Ala Thr
                 10                   15                    20

Asn Ser  Ala Gly Gln Pro Gly  Phe Val Thr Ala Gly  His Cys Gly Thr
             25                   30                    35

Val Gly  Thr Gly Val Thr Ile  Gly Asn Gly Thr Gly  Thr Phe Gln Asn
             40                   45                    50

Ser Val Phe Pro Gly Asn Asp  Ala Ala Phe Val Arg   Gly Thr Ser Asn
55                  60                    65                    70

Phe Thr  Leu Thr Asn Leu Val  Ser Arg Tyr Asn Ser  Gly Gly Tyr Gln
                 75                   80                    85

Ser Val  Thr Gly Thr Ser Gln  Ala Pro Ala Gly Ser  Ala Val Cys Arg
                 90                   95                   100

Ser Gly  Ser Thr Thr Gly Trp  His Cys Gly Thr Ile  Gln Ala Arg Asn
             105                  110                   115

Gln Thr  Val Arg Tyr Pro Gln  Gly Thr Val Tyr Ser  Leu Thr Arg Thr
    120                  125                  130

Asn Val  Cys Ala Glu Pro Gly  Asp Ser Gly Gly Ser  Phe Ile Ser Gly
135                 140                  145                  150

Ser Gln  Ala Gln Gly Val Thr  Ser Gly Gly Ser Gly  Asn Cys Ser Val
             155                  160                  165

Gly Gly  Thr Thr Tyr Tyr Gln  Glu Val Thr Pro Met  Ile Asn Ser Trp
             170                  175                  180

Gly Val  Arg Ile Arg Thr
             185
```

<210> SEQ ID NO 61
<211> LENGTH: 355
<212> TYPE: PRT
<213> ORGANISM: Nocardiopsis alba
<220> FEATURE:
<221> NAME/KEY: mat_peptide

```
<222> LOCATION: (168)..(355)

<400> SEQUENCE: 61

Ala Thr Gly Pro Leu Pro Gln Ser Pro Thr Pro Asp Glu Ala Glu
        -165                -160                -155

Ala Thr Thr Met Val Glu Ala Leu Gln Arg Asp Leu Gly Leu Ser
        -150                -145                -140

Pro Ser Gln Ala Asp Glu Leu Leu Glu Ala Gln Ala Glu Ser Phe
        -135                -130                -125

Glu Ile Asp Glu Ala Ala Thr Ala Ala Ala Ala Asp Ser Tyr Gly
        -120                -115                -110

Gly Ser Ile Phe Asp Thr Asp Ser Leu Thr Leu Thr Val Leu Val Thr
        -105                -100                -95

Asp Ala Ser Ala Val Glu Ala Val Glu Ala Ala Gly Ala Glu Ala Lys
    -90                 -85                 -80

Val Val Ser His Gly Met Glu Gly Leu Glu Glu Ile Val Ala Asp Leu
-75                 -70                 -65                 -60

Asn Ala Ala Asp Ala Gln Pro Gly Val Gly Trp Tyr Pro Asp Ile
            -55                 -50                 -45

His Ser Asp Thr Val Val Leu Glu Val Leu Glu Gly Ser Gly Ala Asp
            -40                 -35                 -30

Val Asp Ser Leu Leu Ala Asp Ala Gly Val Asp Thr Ala Asp Val Lys
    -25                 -20                 -15

Val Glu Ser Thr Thr Glu Gln Pro Glu Leu Tyr Ala Asp Ile Ile Gly
    -10                 -5                  -1   1              5

Gly Leu Ala Tyr Thr Met Gly Gly Arg Cys Ser Val Gly Phe Ala Ala
                    10                  15                  20

Thr Asn Ala Ser Gly Gln Pro Gly Phe Val Thr Ala Gly His Cys Gly
                25                  30                  35

Thr Val Gly Thr Pro Val Ser Ile Gly Asn Gly Gln Gly Val Phe Glu
            40                  45                  50

Arg Ser Val Phe Pro Gly Asn Asp Ser Ala Phe Val Arg Gly Thr Ser
55                  60                  65

Asn Phe Thr Leu Thr Asn Leu Val Ser Arg Tyr Asn Thr Gly Gly Tyr
70                  75                  80                  85

Ala Thr Val Ser Gly Ser Ser Gln Ala Ala Ile Gly Ser Gln Ile Cys
                90                  95                  100

Arg Ser Gly Ser Thr Thr Gly Trp His Cys Gly Thr Val Gln Ala Arg
                105                 110                 115

Gly Gln Thr Val Ser Tyr Pro Gln Gly Thr Val Gln Asn Leu Thr Arg
            120                 125                 130

Thr Asn Val Cys Ala Glu Pro Gly Asp Ser Gly Gly Ser Phe Ile Ser
135                 140                 145

Gly Ser Gln Ala Gln Gly Val Thr Ser Gly Gly Ser Gly Asn Cys Ser
150                 155                 160                 165

Phe Gly Gly Thr Thr Tyr Tyr Gln Glu Val Asn Pro Met Leu Ser Ser
                170                 175                 180

Trp Gly Leu Thr Leu Arg Thr
            185

<210> SEQ ID NO 62
<211> LENGTH: 353
<212> TYPE: PRT
<213> ORGANISM: Nocardiopsis prasina
<220> FEATURE:
<221> NAME/KEY: mat_peptide
```

<222> LOCATION: (166)..(353)

<400> SEQUENCE: 62

```
Ala Thr Gly Pro Leu Pro Gln Ser Pro Thr Pro Glu Ala Asp Ala
-165                -160                -155

Val Ser Met Gln Glu Ala Leu Gln Arg Asp Leu Gly Leu Thr Pro
-150                -145                -140

Leu Glu Ala Asp Glu Leu Leu Ala Ala Gln Asp Thr Ala Phe Glu
-135                -130                -125

Val Asp Glu Ala Ala Ala Ala Ala Ala Gly Asp Ala Tyr Gly Gly
-120                -115                -110

Ser Val Phe Asp Thr Glu Thr Leu Glu Leu Thr Val Leu Val Thr Asp
-105                -100                 -95                -90

Ala Ala Ser Val Glu Ala Val Glu Ala Thr Gly Ala Gly Thr Glu Leu
                -85                 -80                -75

Val Ser Tyr Gly Ile Glu Gly Leu Asp Glu Ile Ile Gln Asp Leu Asn
                -70                 -65                -60

Ala Ala Asp Ala Val Pro Gly Val Val Gly Trp Tyr Pro Asp Val Ala
            -55                 -50                -45

Gly Asp Thr Val Val Leu Glu Val Leu Glu Gly Ser Gly Ala Asp Val
        -40                 -35                -30

Ser Gly Leu Leu Ala Asp Ala Gly Val Asp Ala Ser Ala Val Glu Val
-25                 -20                -15                -10

Thr Ser Ser Ala Gln Pro Glu Leu Tyr Ala Asp Ile Ile Gly Gly Leu
                -5                  -1   1                 5

Ala Tyr Thr Met Gly Gly Arg Cys Ser Val Gly Phe Ala Ala Thr Asn
                10                  15                 20

Ala Ala Gly Gln Pro Gly Phe Val Thr Ala Gly His Cys Gly Arg Val
            25                  30                 35

Gly Thr Gln Val Ser Ile Gly Asn Gly Gln Gly Val Phe Glu Gln Ser
40                  45                  50                 55

Ile Phe Pro Gly Asn Asp Ala Ala Phe Val Arg Gly Thr Ser Asn Phe
                60                  65                 70

Thr Leu Thr Asn Leu Val Ser Arg Tyr Asn Thr Gly Gly Tyr Ala Thr
                75                  80                 85

Val Ala Gly His Asn Gln Ala Pro Ile Gly Ser Ser Val Cys Arg Ser
                90                  95                100

Gly Ser Thr Thr Gly Trp His Cys Gly Thr Ile Gln Ala Arg Gly Gln
105                 110                 115

Ser Val Ser Tyr Pro Glu Gly Thr Val Thr Asn Met Thr Arg Thr Thr
120                 125                 130                135

Val Cys Ala Glu Pro Gly Asp Ser Gly Gly Ser Tyr Ile Ser Gly Asn
                140                 145                150

Gln Ala Gln Gly Val Thr Ser Gly Gly Ser Gly Asn Cys Arg Thr Gly
                155                 160                165

Gly Thr Thr Phe Tyr Gln Glu Val Thr Pro Met Val Asn Ser Trp Gly
                170                 175                180

Val Arg Leu Arg Thr
        185
```

<210> SEQ ID NO 63
<211> LENGTH: 353
<212> TYPE: PRT
<213> ORGANISM: Nocardiopsis prasina
<220> FEATURE:
<221> NAME/KEY: mat_peptide

<222> LOCATION: (166)..(353)

<400> SEQUENCE: 63

```
Ala Thr Gly Pro Leu Pro Gln Ser Pro Thr Pro Glu Ala Asp Ala
-165                -160                -155

Val Ser Met Gln Glu Ala Leu Gln Arg Asp Leu Gly Leu Thr Pro
-150                -145                -140

Leu Glu Ala Asp Glu Leu Leu Ala Ala Gln Asp Thr Ala Phe Glu
-135                -130                -125

Val Asp Glu Ala Ala Ala Glu Ala Ala Gly Asp Ala Tyr Gly Gly
-120                -115                -110

Ser Val Phe Asp Thr Glu Thr Leu Glu Leu Thr Val Leu Val Thr Asp
-105                -100                 -95                 -90

Ser Ala Ala Val Glu Ala Val Glu Ala Thr Gly Ala Gly Thr Glu Leu
                -85                  -80                 -75

Val Ser Tyr Gly Ile Thr Gly Leu Asp Glu Ile Val Glu Glu Leu Asn
                -70                  -65                 -60

Ala Ala Asp Ala Val Pro Gly Val Val Gly Trp Tyr Pro Asp Val Ala
                -55                  -50                 -45

Gly Asp Thr Val Val Leu Glu Val Leu Glu Gly Ser Gly Ala Asp Val
        -40                  -35                 -30

Gly Gly Leu Leu Ala Asp Ala Gly Val Asp Ala Ser Ala Val Glu Val
-25                  -20                  -15                 -10

Thr Thr Thr Glu Gln Pro Glu Leu Tyr Ala Asp Ile Ile Gly Gly Leu
                 -5                  -1   1                   5

Ala Tyr Thr Met Gly Gly Arg Cys Ser Val Gly Phe Ala Ala Thr Asn
                 10                  15                  20

Ala Ala Gly Gln Pro Gly Phe Val Thr Ala Gly His Cys Gly Arg Val
        25                   30                  35

Gly Thr Gln Val Thr Ile Gly Asn Gly Arg Gly Val Phe Glu Gln Ser
40                   45                  50                  55

Ile Phe Pro Gly Asn Asp Ala Ala Phe Val Arg Gly Thr Ser Asn Phe
                 60                  65                  70

Thr Leu Thr Asn Leu Val Ser Arg Tyr Asn Thr Gly Gly Tyr Ala Thr
                 75                  80                  85

Val Ala Gly His Asn Gln Ala Pro Ile Gly Ser Ser Val Cys Arg Ser
        90                   95                 100

Gly Ser Thr Thr Gly Trp His Cys Gly Thr Ile Gln Ala Arg Gly Gln
105                 110                  115

Ser Val Ser Tyr Pro Glu Gly Thr Val Thr Asn Met Thr Arg Thr Thr
120                 125                  130                 135

Val Cys Ala Glu Pro Gly Asp Ser Gly Gly Ser Tyr Ile Ser Gly Asn
                140                  145                 150

Gln Ala Gln Gly Val Thr Ser Gly Gly Ser Gly Asn Cys Arg Thr Gly
                155                  160                 165

Gly Thr Thr Phe Tyr Gln Glu Val Thr Pro Met Val Asn Ser Trp Gly
        170                  175                 180

Val Arg Leu Arg Thr
        185
```

<210> SEQ ID NO 64
<211> LENGTH: 439
<212> TYPE: PRT
<213> ORGANISM: Peniophora lycii
<220> FEATURE:
<221> NAME/KEY: mat_peptide

<222> LOCATION: (31)..(439)

<400> SEQUENCE: 64

```
Met Val Ser Ser Ala Phe Ala Pro Ser Ile Leu Leu Ser Leu Met Ser
-30                 -25                 -20                 -15
Ser Leu Ala Leu Ser Thr Gln Phe Ser Phe Val Ala Ala Gln Leu Pro
                -10                  -5                  -1   1
Ile Pro Ala Gln Asn Thr Ser Asn Trp Gly Pro Tyr Asp Pro Phe Phe
             5                  10                  15
Pro Val Glu Pro Tyr Ala Ala Pro Pro Glu Gly Cys Thr Val Thr Gln
     20                  25                  30
Val Asn Leu Ile Gln Arg His Gly Ala Arg Trp Pro Thr Ser Gly Ala
 35                  40                  45                  50
Arg Ser Arg Gln Val Ala Val Ala Lys Ile Gln Met Ala Arg Pro
                 55                  60                  65
Phe Thr Asp Pro Lys Tyr Glu Phe Leu Asn Asp Phe Val Tyr Lys Phe
             70                  75                  80
Gly Val Ala Asp Leu Leu Pro Phe Gly Ala Asn Gln Ser His Gln Thr
             85                  90                  95
Gly Thr Asp Met Tyr Thr Arg Tyr Ser Thr Leu Phe Glu Gly Gly Asp
            100                 105                 110
Val Pro Phe Val Arg Ala Ala Gly Asp Gln Arg Val Val Asp Ser Ser
115                 120                 125                 130
Thr Asn Trp Thr Ala Gly Phe Gly Asp Ala Ser Gly Glu Thr Val Leu
                135                 140                 145
Pro Thr Leu Gln Val Val Leu Gln Glu Gly Asn Cys Thr Leu Cys
                150                 155                 160
Asn Asn Met Cys Pro Asn Glu Val Asp Gly Asp Glu Ser Thr Thr Trp
            165                 170                 175
Leu Gly Val Phe Ala Pro Asn Ile Thr Ala Arg Leu Asn Ala Ala Ala
    180                 185                 190
Pro Ser Ala Asn Leu Ser Asp Ser Asp Ala Leu Thr Leu Met Asp Met
195                 200                 205                 210
Cys Pro Phe Asp Thr Leu Ser Ser Gly Asn Ala Ser Pro Phe Cys Asp
                215                 220                 225
Leu Phe Thr Ala Glu Glu Tyr Val Ser Tyr Glu Tyr Tyr Tyr Asp Leu
            230                 235                 240
Asp Lys Tyr Tyr Gly Thr Gly Pro Gly Asn Ala Leu Gly Pro Val Gln
        245                 250                 255
Gly Val Gly Tyr Val Asn Glu Leu Leu Ala Arg Leu Thr Gly Gln Ala
    260                 265                 270
Val Arg Asp Glu Thr Gln Thr Asn Arg Thr Leu Asp Ser Asp Pro Ala
275                 280                 285                 290
Thr Phe Pro Leu Asn Arg Thr Phe Tyr Ala Asp Phe Ser His Asp Asn
                295                 300                 305
Thr Met Val Pro Ile Phe Ala Ala Leu Gly Leu Phe Asn Ala Thr Ala
            310                 315                 320
Leu Asp Pro Leu Lys Pro Asp Glu Asn Arg Leu Trp Val Asp Ser Lys
        325                 330                 335
Leu Val Pro Phe Ser Gly His Met Thr Val Glu Lys Leu Ala Cys Ser
    340                 345                 350
Gly Lys Glu Ala Val Arg Val Leu Val Asn Asp Ala Val Gln Pro Leu
355                 360                 365                 370
Glu Phe Cys Gly Gly Val Asp Gly Val Cys Glu Leu Ser Ala Phe Val
```

```
                 375                 380                 385
Glu Ser Gln Thr Tyr Ala Arg Glu Asn Gly Gln Gly Asp Phe Ala Lys
            390                 395                 400

Cys Gly Phe Val Pro Ser Glu
        405
```

<210> SEQ ID NO 65
<211> LENGTH: 39
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(39)

<400> SEQUENCE: 65

```
Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35
```

<210> SEQ ID NO 66
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 66
catagcacca tggaaaggag acgtccccga cccccatatt tgcc         44

<210> SEQ ID NO 67
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 67
catagcacca tggatgaaag gagacgtccc cgaccccat atttgcc         47

<210> SEQ ID NO 68
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 68
catagcacca tggacgatga aaggagacgt ccccgacccc catatttgcc     50

<210> SEQ ID NO 69
<211> LENGTH: 53
<212> TYPE: DNA
<213> ORGANISM: Artificial Sequence -continued

```
<220> FEATURE:
<223> OTHER INFORMATION: Primer
<220> FEATURE:
<221> NAME/KEY: misc_feature
<223> OTHER INFORMATION: Primer

<400> SEQUENCE: 69
catagcacca tggatgacga tgaaaggaga cgtccccgac ccccatattt gcc          53

<210> SEQ ID NO 70
<211> LENGTH: 56
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 70
catagcacca tggacgatga cgatgaaagg agacgtcccc gaccccata tttgcc       56

<210> SEQ ID NO 71
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 71
ccataagatt agcggatcct acc                                          23

<210> SEQ ID NO 72
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 72
ctctcatccg ccaaaacagc c                                            21

<210> SEQ ID NO 73
<211> LENGTH: 18
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(18)

<400> SEQUENCE: 73

Lys Asn Leu Arg Arg Ile Ile Arg Lys Gly Ile His Ile Ile Lys Lys
1               5                   10                  15

Tyr Gly

<210> SEQ ID NO 74
<211> LENGTH: 51
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<223> OTHER INFORMATION: Primer

<400> SEQUENCE: 74
aggggtatcg atggctaaga gagaagccga aaggagacgt ccccgacccc c          51

<210> SEQ ID NO 75
<211> LENGTH: 54
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 75
aggggtatcg atggctaaga gagaagccga tgaaaggaga cgtccccgac cccc        54

<210> SEQ ID NO 76
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 76
aggggtatcg atggctaaga gagaagccga cgatgaaagg agacgtcccc gaccccc     57

<210> SEQ ID NO 77
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 77
aggggtatcg atggctaaga gagaagccga tgacgatgaa aggagacgtc cccgaccccc  60

<210> SEQ ID NO 78
<211> LENGTH: 63
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 78
aggggtatcg atggctaaga gagaagccga cgatgacgat gaaaggagac gtccccgacc  60
ccc                                                               63

<210> SEQ ID NO 79
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Linker
```

```
<400> SEQUENCE: 79

Pro Glu Pro Thr
1

<210> SEQ ID NO 80
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Linker

<400> SEQUENCE: 80

Glu Pro Thr Pro
1

<210> SEQ ID NO 81
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Linker

<400> SEQUENCE: 81

Pro Thr Glu Pro
1

<210> SEQ ID NO 82
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Linker

<400> SEQUENCE: 82

Thr Pro Glu Pro
1

<210> SEQ ID NO 83
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: linker

<400> SEQUENCE: 83

Ile Glu Gly Arg
1

<210> SEQ ID NO 84
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Extension
```

```
<400> SEQUENCE: 84

Gln Ser His Val Gln Ser Ala Pro
1               5

<210> SEQ ID NO 85
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Extension

<400> SEQUENCE: 85

Gln Ser Ala Pro
1

<210> SEQ ID NO 86
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Cleavage linker
<220> FEATURE:
<221> NAME/KEY: Misc_feature
<222> LOCATION: (1)..(1)
<223> OTHER INFORMATION: Xaa denotes any amino acid
<220> FEATURE:
<221> NAME/KEY: Misc_feature
<222> LOCATION: (6)..(6)
<223> OTHER INFORMATION: Xaa denotes any amino acid

<400> SEQUENCE: 86

Xaa Asp Asp Asp Lys Xaa
1               5

<210> SEQ ID NO 87
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Cleavage linker
<220> FEATURE:
<221> NAME/KEY: Misc_feature
<222> LOCATION: (1)..(1)
<223> OTHER INFORMATION: Xaa denotes any amino acid
<220> FEATURE:
<221> NAME/KEY: Misc_feature
<222> LOCATION: (4)..(4)
<223> OTHER INFORMATION: Xaa denotes any amino acid

<400> SEQUENCE: 87

Xaa Lys Arg Xaa
1

<210> SEQ ID NO 88
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Cleavage linker
```

```
<220> FEATURE:
<221> NAME/KEY: Misc_feature
<222> LOCATION: (1)..(1)
<223> OTHER INFORMATION: Xaa denotes any amino acid
<220> FEATURE:
<221> NAME/KEY: Misc_feature
<222> LOCATION: (6)..(6)
<223> OTHER INFORMATION: Xaa denotes any amino acid

<400> SEQUENCE: 88

Xaa Ile Glu Gly Arg Xaa
1               5

<210> SEQ ID NO 89
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Cleavage linker
<220> FEATURE:
<221> NAME/KEY: Misc_feature
<222> LOCATION: (2)..(2)
<223> OTHER INFORMATION: Xaa denotes any amino acid
<220> FEATURE:
<221> NAME/KEY: Misc_feature
<222> LOCATION: (5)..(6)
<223> OTHER INFORMATION: Xaa denotes any amino acid

<400> SEQUENCE: 89

Pro Xaa Gly Pro Xaa Xaa
1               5

<210> SEQ ID NO 90
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Cleavage linker
<220> FEATURE:
<221> NAME/KEY: Misc_feature
<222> LOCATION: (1)..(1)
<223> OTHER INFORMATION: Xaa denotes any amino acid
<220> FEATURE:
<221> NAME/KEY: Misc_feature
<222> LOCATION: (8)..(8)
<223> OTHER INFORMATION: Xaa denotes any amino acid

<400> SEQUENCE: 90

Xaa Gly Val Arg Gly Pro Arg Xaa
1               5

<210> SEQ ID NO 91
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Cleavage linker
<220> FEATURE:
<221> NAME/KEY: Misc_feature
<222> LOCATION: (4)..(4)
<223> OTHER INFORMATION: Xaa denotes any amino acid

<400> SEQUENCE: 91

Ser Asn Gly Xaa
```

```
<210> SEQ ID NO 92
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 92

Asp Asp Glu Glu Glu
1               5

<210> SEQ ID NO 93
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection Peptide

<400> SEQUENCE: 93

Asp Asp Asp Glu Glu
1               5

<210> SEQ ID NO 94
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 94

Asp Asp Asp Asp Glu
1               5

<210> SEQ ID NO 95
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 95

Glu Glu Asp Asp Glu
1               5

<210> SEQ ID NO 96
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 96

Asp Asp Glu Glu Asp
```

<210> SEQ ID NO 97
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 97

Glu Asp Glu Asp Glu
1               5

<210> SEQ ID NO 98
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 98

Asp Asp Asp Glu Glu Glu
1               5

<210> SEQ ID NO 99
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 99

Asp Glu Asp Glu Asp Glu
1               5

<210> SEQ ID NO 100
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 100

Glu Glu Asp Asp Glu Glu
1               5

<210> SEQ ID NO 101
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 101

Asp Asp Asp Asp Asp Pro

<210> SEQ ID NO 102
<211> LENGTH: 7
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 102

Glu Glu Glu Glu Glu Asp Pro
1               5

<210> SEQ ID NO 103
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 103

Asp Asp Asp Glu
1

<210> SEQ ID NO 104
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 104

Asp Glu Asp Glu Asp Glu Asp Pro
1               5

<210> SEQ ID NO 105
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 105

Asp Asp Asp Gly Gly Glu Glu Glu Gly Gly Asp Asp Asp Pro
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: Protection peptide

<400> SEQUENCE: 106

Asp Asp Asp Gly Gly Asp Asp Asp Pro Pro Asp Asp Asp Glu

<210> SEQ ID NO 107
<211> LENGTH: 31
<212> TYPE: DNA
<213> ORGANISM: Artificial Sequence
<220> FEATURE:
<223> OTHER INFORMATION: Primer

<400> SEQUENCE: 107
tatagagctc cattgaaagg ggaggagaat c                                    31

<210> SEQ ID NO 108
<211> LENGTH: 33
<212> TYPE: DNA
<213> ORGANISM: Artificial Sequence
<220> FEATURE:
<223> OTHER INFORMATION: Primer

<400> SEQUENCE: 108
tatactgcag aatgaggcag caagaagatg agc                                  33

<210> SEQ ID NO 109
<211> LENGTH: 33
<212> TYPE: DNA
<213> ORGANISM: Artificial Sequence
<220> FEATURE:
<223> OTHER INFORMATION: Primer

<400> SEQUENCE: 109
tatactgcag ccgcggcagc ttctgcctta aac                                  33

<210> SEQ ID NO 110
<211> LENGTH: 32
<212> TYPE: DNA
<213> ORGANISM: Artificial Sequence
<220> FEATURE:
<223> OTHER INFORMATION: Primer

<400> SEQUENCE: 110
tatagctagc tggattgatt ttgccgactc cg                                   32

<210> SEQ ID NO 111
<211> LENGTH: 1227
<212> TYPE: DNA
<213> ORGANISM: Artificial Sequence
<220> FEATURE:
<223> OTHER INFORMATION: DNA fragment (PP1223-9 Sac1 Mlu1)
<220> FEATURE:
<221> NAME/KEY: CDS
<222> LOCATION: (28)..(1218)
<220> FEATURE:
<221> NAME/KEY: misc_feature
<222> LOCATION: (115)..(1056)
<223> OTHER INFORMATION: Pectate lyase
<220> FEATURE:
<221> NAME/KEY: mat_peptide
<222> LOCATION: (115)..()
<220> FEATURE:
<221> NAME/KEY: misc_feature
<222> LOCATION: (1066)..(1218)
<223> OTHER INFORMATION: AFP

<400> SEQUENCE: 111
gagctccatt gaaaggggag gagaatc atg aaa caa caa aaa cgg ctt tac gcc     54
                            Met Lys Gln Gln Lys Arg Leu Tyr Ala
                                            -25 cga ttg ctg acg ctg tta ttt gcg ctc atc ttc ttg ctg cct cat tct     102
Arg Leu Leu Thr Leu Leu Phe Ala Leu Ile Phe Leu Leu Pro His Ser

```
              -20              -15              -10               -5
gca gcc gcg gca gct tct gcc tta aac tcg ggc aaa gta aat ccg ctt        150
Ala Ala Ala Ala Ala Ser Ala Leu Asn Ser Gly Lys Val Asn Pro Leu
            -1  1                   5                  10 gcc gac ttc agc tta aaa ggc ttt gcc gca cta aac ggc gga aca acg        198
Ala Asp Phe Ser Leu Lys Gly Phe Ala Ala Leu Asn Gly Gly Thr Thr
        15                  20                  25 ggc gga gaa ggc ggt cag acg gta acc gta aca acg gga gat cag ctg        246
Gly Gly Glu Gly Gly Gln Thr Val Thr Val Thr Thr Gly Asp Gln Leu
    30                  35                  40 att gcg gca tta aaa aat aag aat gca aat acg cct tta aaa att tat        294
Ile Ala Ala Leu Lys Asn Lys Asn Ala Asn Thr Pro Leu Lys Ile Tyr
45                  50                  55                  60 gtc aac ggc acc att aca aca tca aat aca tcc gca tca aag att gac        342
Val Asn Gly Thr Ile Thr Thr Ser Asn Thr Ser Ala Ser Lys Ile Asp
                65                  70                  75 gtc aaa gac gtg tca aac gta tcg att gtc gga tca ggg acc aaa ggg        390
Val Lys Asp Val Ser Asn Val Ser Ile Val Gly Ser Gly Thr Lys Gly
        80                  85                  90 gaa ctc aaa ggg atc ggc atc aaa ata tgg cgg gcc aac aac atc atc        438
Glu Leu Lys Gly Ile Gly Ile Lys Ile Trp Arg Ala Asn Asn Ile Ile
    95                  100                 105 atc cgc aac ttg aaa att cac gag gtc gcc tca ggc gat aaa gac gcg        486
Ile Arg Asn Leu Lys Ile His Glu Val Ala Ser Gly Asp Lys Asp Ala
110                 115                 120 atc ggc att gaa ggc cct tct aaa aac att tgg gtt gat cat aat gag        534
Ile Gly Ile Glu Gly Pro Ser Lys Asn Ile Trp Val Asp His Asn Glu
125                 130                 135                 140 ctt tac cac agc ctg aac gtt gac aaa gat tac tat gac gga tta ttt        582
Leu Tyr His Ser Leu Asn Val Asp Lys Asp Tyr Tyr Asp Gly Leu Phe
            145                 150                 155 gac gtc aaa aga gat gcg gaa tat att aca ttc tct tgg aac tat gtg        630
Asp Val Lys Arg Asp Ala Glu Tyr Ile Thr Phe Ser Trp Asn Tyr Val
        160                 165                 170 cac gat gga tgg aaa tca atg ctg atg ggt tca tcg gac agc gat aat        678
His Asp Gly Trp Lys Ser Met Leu Met Gly Ser Ser Asp Ser Asp Asn
    175                 180                 185 tac aac agg acg att aca ttc cat cat aac tgg ttt gag aat ctg aat        726
Tyr Asn Arg Thr Ile Thr Phe His His Asn Trp Phe Glu Asn Leu Asn
190                 195                 200 tcg cgt gtg ccg tca ttc cgt ttc gga gaa ggc cat att tac aac aac        774
Ser Arg Val Pro Ser Phe Arg Phe Gly Glu Gly His Ile Tyr Asn Asn
205                 210                 215                 220 tat ttc aat aaa atc atc gac agc gga att aat tcg agg atg ggc gcg        822
Tyr Phe Asn Lys Ile Ile Asp Ser Gly Ile Asn Ser Arg Met Gly Ala
            225                 230                 235 cgc atc aga att gag aac aac ctc ttt gaa aac gcc aaa gat ccg att        870
Arg Ile Arg Ile Glu Asn Asn Leu Phe Glu Asn Ala Lys Asp Pro Ile
        240                 245                 250 gtc tct tgg tac agc agt tca ccg ggc tat tgg cat gta tcc aac aac        918
Val Ser Trp Tyr Ser Ser Ser Pro Gly Tyr Trp His Val Ser Asn Asn
    255                 260                 265 aaa ttt gta aac tct agg ggc agt atg ccg act acc tct act aca acc        966
Lys Phe Val Asn Ser Arg Gly Ser Met Pro Thr Thr Ser Thr Thr Thr
270                 275                 280 tat aat ccg cca tac agc tac tca ctc gac aat gtc gac aat gta aaa       1014
Tyr Asn Pro Pro Tyr Ser Tyr Ser Leu Asp Asn Val Asp Asn Val Lys
285                 290                 295                 300 tca atc gtc aag caa aat gcc gga gtc ggc aaa atc aat cca gct agc       1062
Ser Ile Val Lys Gln Asn Ala Gly Val Gly Lys Ile Asn Pro Ala Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 305 |     |     |     |     | 310 |     |     |     |     | 315 |     |      |
| gaa | gcc | acc | tac | ccc | ggc | aag | tgc | tac | aag | aag | gac | aac | atc | tgc | aag | 1110 |
| Glu | Ala | Thr | Tyr | Pro | Gly | Lys | Cys | Tyr | Lys | Lys | Asp | Asn | Ile | Cys | Lys |      |
|     |     | 320 |     |     |     |     | 325 |     |     |     |     | 330 |     |     |     |      |
| tac | aag | gcc | cag | tcc | ggc | aag | acc | ggc | atc | tgc | aag | tgc | tac | gtc | aag | 1158 |
| Tyr | Lys | Ala | Gln | Ser | Gly | Lys | Thr | Gly | Ile | Cys | Lys | Cys | Tyr | Val | Lys |      |
|     | 335 |     |     |     |     | 340 |     |     |     |     | 345 |     |     |     |     |      |
| cgc | tgc | ccc | cgc | gac | ggc | gcc | aag | tgc | gac | ctc | gac | tcc | tac | aag | ggc | 1206 |
| Arg | Cys | Pro | Arg | Asp | Gly | Ala | Lys | Cys | Asp | Leu | Asp | Ser | Tyr | Lys | Gly |      |
| 350 |     |     |     |     | 355 |     |     |     |     | 360 |     |     |     |     |     |      |
| aag | tgc | cac | tgc | tagacgcgt |     |     |     |     |     |     |     |     |     |     |     | 1227 |
| Lys | Cys | His | Cys |     |     |     |     |     |     |     |     |     |     |     |     |      |
| 365 |     |     |     |     |     |     |     |     |     |     |     |     |     |     |     |      |

<210> SEQ ID NO 112
<211> LENGTH: 397
<212> TYPE: PRT
<213> ORGANISM: Artificial Sequence
<220> FEATURE:
<223> OTHER INFORMATION: Synthetic Construct

<400> SEQUENCE: 112

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Ala Ser Ala
        -10                  -5              -1   1

Leu Asn Ser Gly Lys Val Asn Pro Leu Ala Asp Phe Ser Leu Lys Gly
     5                  10                  15

Phe Ala Ala Leu Asn Gly Gly Thr Thr Gly Gly Glu Gly Gly Gln Thr
20                  25                  30                  35

Val Thr Val Thr Thr Gly Asp Gln Leu Ile Ala Ala Leu Lys Asn Lys
                40                  45                  50

Asn Ala Asn Thr Pro Leu Lys Ile Tyr Val Asn Gly Thr Ile Thr Thr
                55                  60                  65

Ser Asn Thr Ser Ala Ser Lys Ile Asp Val Lys Asp Val Ser Asn Val
        70                  75                  80

Ser Ile Val Gly Ser Gly Thr Lys Gly Glu Leu Lys Gly Ile Gly Ile
    85                  90                  95

Lys Ile Trp Arg Ala Asn Asn Ile Ile Ile Arg Asn Leu Lys Ile His
100                 105                 110                 115

Glu Val Ala Ser Gly Asp Lys Asp Ala Ile Gly Ile Glu Gly Pro Ser
                120                 125                 130

Lys Asn Ile Trp Val Asp His Asn Glu Leu Tyr His Ser Leu Asn Val
                135                 140                 145

Asp Lys Asp Tyr Tyr Asp Gly Leu Phe Asp Val Lys Arg Asp Ala Glu
        150                 155                 160

Tyr Ile Thr Phe Ser Trp Asn Tyr Val His Asp Gly Trp Lys Ser Met
    165                 170                 175

Leu Met Gly Ser Ser Asp Ser Asp Asn Tyr Asn Arg Thr Ile Thr Phe
180                 185                 190                 195

His His Asn Trp Phe Glu Asn Leu Asn Ser Arg Val Pro Ser Phe Arg
                200                 205                 210

Phe Gly Glu Gly His Ile Tyr Asn Asn Tyr Phe Asn Lys Ile Ile Asp
                215                 220                 225

Ser Gly Ile Asn Ser Arg Met Gly Ala Arg Ile Arg Ile Glu Asn Asn
        230                 235                 240

Leu Phe Glu Asn Ala Lys Asp Pro Ile Val Ser Trp Tyr Ser Ser Ser

```
              245                 250                 255
Pro Gly Tyr Trp His Val Ser Asn Asn Lys Phe Val Asn Ser Arg Gly
260                 265                 270                 275

Ser Met Pro Thr Thr Ser Thr Thr Thr Tyr Asn Pro Pro Tyr Ser Tyr
                280                 285                 290

Ser Leu Asp Asn Val Asp Asn Val Lys Ser Ile Val Lys Gln Asn Ala
                295                 300                 305

Gly Val Gly Lys Ile Asn Pro Ala Ser Glu Ala Thr Tyr Pro Gly Lys
                310                 315                 320

Cys Tyr Lys Lys Asp Asn Ile Cys Lys Tyr Lys Ala Gln Ser Gly Lys
                325                 330                 335

Thr Gly Ile Cys Lys Cys Tyr Val Lys Arg Cys Pro Arg Asp Gly Ala
340                 345                 350                 355

Lys Cys Asp Leu Asp Ser Tyr Lys Gly Lys Cys His Cys
                360                 365

<210> SEQ ID NO 113
<211> LENGTH: 26
<212> TYPE: DNA
<213> ORGANISM: Artificial Sequence
<220> FEATURE:
<223> OTHER INFORMATION: Primer

<400> SEQUENCE: 113
tataacgcgt ctagcagtgg cacttg                                          26

<210> SEQ ID NO 114
<211> LENGTH: 1297
<212> TYPE: DNA
<213> ORGANISM: Artificial Sequence
<220> FEATURE:
<223> OTHER INFORMATION: DNA fragment (PP1331-2 Sac1 Mlu1)
<220> FEATURE:
<221> NAME/KEY: CDS
<222> LOCATION: (27)..(1289)
<220> FEATURE:
<221> NAME/KEY: mat_peptide
<222> LOCATION: (114)..(1289)
<220> FEATURE:
<221> NAME/KEY: misc_feature
<222> LOCATION: (114)..(1055)
<223> OTHER INFORMATION: Pectate lyase
<220> FEATURE:
<221> NAME/KEY: misc_feature
<222> LOCATION: (1236)..(1289)
<223> OTHER INFORMATION: G10 novispirin

<400> SEQUENCE: 114
gagctcattg aaagggagg agaatc atg aaa caa caa aaa cgg ctt tac gcc       53
                            Met Lys Gln Gln Lys Arg Leu Tyr Ala
                                             -25 cga ttg ctg acg ctg tta ttt gcg ctc atc ttc ttg ctg cct cat tct      101
Arg Leu Leu Thr Leu Leu Phe Ala Leu Ile Phe Leu Leu Pro His Ser
-20                 -15                 -10                  -5 gca gcc gcg gca gct tct gcc tta aac tcg ggc aaa gta aat ccg ctt      149
Ala Ala Ala Ala Ala Ser Ala Leu Asn Ser Gly Lys Val Asn Pro Leu
                -1  1               5                  10 gcc gac ttc agc tta aaa ggc ttt gcc gca cta aac ggc gga aca acg      197
Ala Asp Phe Ser Leu Lys Gly Phe Ala Ala Leu Asn Gly Gly Thr Thr
            15                  20                  25 ggc gga gaa ggc ggt cag acg gta acc gta aca acg gga gat cag ctg      245
Gly Gly Glu Gly Gly Gln Thr Val Thr Val Thr Thr Gly Asp Gln Leu
        30                  35                  40 att gcg gca tta aaa aat aag aat gca aat acg cct tta aaa att tat      293
```

```
                -continued

Ile Ala Ala Leu Lys Asn Lys Asn Ala Asn Thr Pro Leu Lys Ile Tyr
45              50                  55                  60 gtc aac ggc acc att aca aca tca aat aca tcc gca tca aag att gac       341
Val Asn Gly Thr Ile Thr Thr Ser Asn Thr Ser Ala Ser Lys Ile Asp
                65                  70                  75 gtc aaa gac gtg tca aac gta tcg att gtc gga tca ggg acc aaa ggg       389
Val Lys Asp Val Ser Asn Val Ser Ile Val Gly Ser Gly Thr Lys Gly
                80                  85                  90 gaa ctc aaa ggg atc ggc atc aaa ata tgg cgg gcc aat aac atc atc       437
Glu Leu Lys Gly Ile Gly Ile Lys Ile Trp Arg Ala Asn Asn Ile Ile
                95                  100                 105 atc cgc aac ttg aaa att cac gag gtc gcc tca ggc gat aaa gac gcg       485
Ile Arg Asn Leu Lys Ile His Glu Val Ala Ser Gly Asp Lys Asp Ala
        110                 115                 120 atc ggc att gaa ggc cct tct aaa aac att tgg gtt gat cat aat gag       533
Ile Gly Ile Glu Gly Pro Ser Lys Asn Ile Trp Val Asp His Asn Glu
125                 130                 135                 140 ctt tac cac agc ctg aac gtt gac aaa gat tac tat gac gga tta ttt       581
Leu Tyr His Ser Leu Asn Val Asp Lys Asp Tyr Tyr Asp Gly Leu Phe
                145                 150                 155 gac gtc aaa aga gat gcg gaa tat att aca ttc tct tgg aac tat gtg       629
Asp Val Lys Arg Asp Ala Glu Tyr Ile Thr Phe Ser Trp Asn Tyr Val
                160                 165                 170 cac gat gga tgg aaa tca atg ctg atg ggt tca tcg gac agc gat aat       677
His Asp Gly Trp Lys Ser Met Leu Met Gly Ser Ser Asp Ser Asp Asn
                175                 180                 185 tac aac agg acg att aca ttc cat cat aac tgg ttt gag aat ctg aat       725
Tyr Asn Arg Thr Ile Thr Phe His His Asn Trp Phe Glu Asn Leu Asn
190                 195                 200 tcg cgt gtg tcg tca ttc cgt ttc gga gaa ggc cat att tac aac aac       773
Ser Arg Val Ser Ser Phe Arg Phe Gly Glu Gly His Ile Tyr Asn Asn
205                 210                 215                 220 tat ttc aat aaa atc atc gac agc gga att aat tcg agg atg ggc gcg       821
Tyr Phe Asn Lys Ile Ile Asp Ser Gly Ile Asn Ser Arg Met Gly Ala
                225                 230                 235 cgc atc aga att gag aac aac ctc ttt gaa aac gcc aaa gat ccg att       869
Arg Ile Arg Ile Glu Asn Asn Leu Phe Glu Asn Ala Lys Asp Pro Ile
                240                 245                 250 gtc tct tgg tac agc agt tca ccg ggc tat tgg cat gta tcc aac aac       917
Val Ser Trp Tyr Ser Ser Ser Pro Gly Tyr Trp His Val Ser Asn Asn
        255                 260                 265 aaa ttt gta aac tct agg ggc agt atg ccg act acc tct act aca acc       965
Lys Phe Val Asn Ser Arg Gly Ser Met Pro Thr Thr Ser Thr Thr Thr
270                 275                 280 tat aat ccg cca tac agc tac tca ctc gac aat gtc gac aat gta aaa      1013
Tyr Asn Pro Pro Tyr Ser Tyr Ser Leu Asp Asn Val Asp Asn Val Lys
285                 290                 295                 300 tca atc gtc aag caa aat gcc gga gtc ggc aaa atc aat cca gct agc      1061
Ser Ile Val Lys Gln Asn Ala Gly Val Gly Lys Ile Asn Pro Ala Ser
                305                 310                 315 ttg gat aaa aga gag gct gaa gct tgt gag gaa gag aga aat gca gaa      1109
Leu Asp Lys Arg Glu Ala Glu Ala Cys Glu Glu Glu Arg Asn Ala Glu
                320                 325                 330 gaa gaa aga aga gat gaa cca gat gaa agg gat gct caa gtg gaa cat      1157
Glu Glu Arg Arg Asp Glu Pro Asp Glu Arg Asp Ala Gln Val Glu His
                335                 340                 345 aat gcg cgc gag gct gaa gct gat gcg gaa gcg gtg ggc ccg gaa gcg      1205
Asn Ala Arg Glu Ala Glu Ala Asp Ala Glu Ala Val Gly Pro Glu Ala
        350                 355                 360 ttt gcg gat gaa gat ctg gat cca tgg gaa aag aac ctc aga cga atc      1253
```

```
Phe Ala Asp Glu Asp Leu Asp Pro Trp Glu Lys Asn Leu Arg Arg Ile
365                 370                 375                 380 ata agg aaa ggt ata cac atc att aag aaa tac gga taacgcgt              1297
Ile Arg Lys Gly Ile His Ile Ile Lys Lys Tyr Gly
                385                 390
```

<210> SEQ ID NO 115
<211> LENGTH: 421
<212> TYPE: PRT
<213> ORGANISM: Artificial Sequence
<220> FEATURE:
<223> OTHER INFORMATION: Synthetic Construct

<400> SEQUENCE: 115

```
Met Lys Gln Gln Lys Arg Leu Tyr Ala Arg Leu Leu Thr Leu Leu Phe
                -25                 -20                 -15

Ala Leu Ile Phe Leu Leu Pro His Ser Ala Ala Ala Ala Ser Ala
            -10                  -5              -1   1

Leu Asn Ser Gly Lys Val Asn Pro Leu Ala Asp Phe Ser Leu Lys Gly
        5                   10                  15

Phe Ala Ala Leu Asn Gly Gly Thr Thr Gly Gly Glu Gly Gly Gln Thr
20                  25                  30                  35

Val Thr Val Thr Thr Gly Asp Gln Leu Ile Ala Ala Leu Lys Asn Lys
                40                  45                  50

Asn Ala Asn Thr Pro Leu Lys Ile Tyr Val Asn Gly Thr Ile Thr Thr
                55                  60                  65

Ser Asn Thr Ser Ala Ser Lys Ile Asp Val Lys Asp Val Ser Asn Val
            70                  75                  80

Ser Ile Val Gly Ser Gly Thr Lys Gly Glu Leu Lys Gly Ile Gly Ile
85                  90                  95

Lys Ile Trp Arg Ala Asn Asn Ile Ile Ile Arg Asn Leu Lys Ile His
100                 105                 110                 115

Glu Val Ala Ser Gly Asp Lys Asp Ala Ile Gly Ile Glu Gly Pro Ser
                120                 125                 130

Lys Asn Ile Trp Val Asp His Asn Glu Leu Tyr His Ser Leu Asn Val
                135                 140                 145

Asp Lys Asp Tyr Tyr Asp Gly Leu Phe Asp Val Lys Arg Asp Ala Glu
            150                 155                 160

Tyr Ile Thr Phe Ser Trp Asn Tyr Val His Asp Gly Trp Lys Ser Met
165                 170                 175

Leu Met Gly Ser Ser Asp Ser Asp Asn Tyr Asn Arg Thr Ile Thr Phe
180                 185                 190                 195

His His Asn Trp Phe Glu Asn Leu Asn Ser Arg Val Ser Ser Phe Arg
                200                 205                 210

Phe Gly Glu Gly His Ile Tyr Asn Asn Tyr Phe Asn Lys Ile Ile Asp
            215                 220                 225

Ser Gly Ile Asn Ser Arg Met Gly Ala Arg Ile Arg Ile Glu Asn Asn
                230                 235                 240

Leu Phe Glu Asn Ala Lys Asp Pro Ile Val Ser Trp Tyr Ser Ser Ser
245                 250                 255

Pro Gly Tyr Trp His Val Ser Asn Asn Lys Phe Val Asn Ser Arg Gly
260                 265                 270                 275

Ser Met Pro Thr Thr Ser Thr Thr Tyr Asn Pro Pro Tyr Ser Tyr
            280                 285                 290

Ser Leu Asp Asn Val Asp Asn Val Lys Ser Ile Val Lys Gln Asn Ala
                295                 300                 305
```

```
Gly Val Gly Lys Ile Asn Pro Ala Ser Leu Asp Lys Arg Glu Ala Glu
            310                 315                 320
Ala Cys Glu Glu Glu Arg Asn Ala Glu Glu Arg Arg Asp Glu Pro
    325                 330                 335
Asp Glu Arg Asp Ala Gln Val Glu His Asn Ala Arg Glu Ala Glu Ala
340                 345                 350                 355
Asp Ala Glu Ala Val Gly Pro Glu Ala Phe Ala Asp Glu Asp Leu Asp
            360                 365                 370
Pro Trp Glu Lys Asn Leu Arg Arg Ile Ile Arg Lys Gly Ile His Ile
            375                 380                 385
Ile Lys Lys Tyr Gly
            390
```

<210> SEQ ID NO 116
<211> LENGTH: 28
<212> TYPE: DNA
<213> ORGANISM: Artificial Sequence
<220> FEATURE:
<223> OTHER INFORMATION: Primer

<400> SEQUENCE: 116
tataacgcgt tatccgtatt tcttaatg                                         28

<210> SEQ ID NO 117
<211> LENGTH: 53
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(5)
<223> OTHER INFORMATION: Quenching domain
<220> FEATURE:
<221> NAME/KEY: MISC_FEATURE
<222> LOCATION: (6)..(14)
<223> OTHER INFORMATION: Linker
<220> FEATURE:
<221> NAME/KEY: MISC_FEATURE
<222> LOCATION: (15)..()
<223> OTHER INFORMATION: PR39

<400> SEQUENCE: 117

```
Asp Asp Asp Asp Glu Gly Gly Gly Gly Gly Gly Gly Glu Arg Arg
1               5                   10                  15
Arg Pro Arg Pro Pro Tyr Leu Pro Arg Pro Arg Pro Pro Phe Phe
            20                  25                  30
Pro Pro Arg Leu Pro Pro Arg Ile Pro Pro Gly Phe Pro Pro Arg Phe
            35                  40                  45
Pro Pro Arg Phe Pro
            50
```

<210> SEQ ID NO 118
<211> LENGTH: 57
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(5)
<223> OTHER INFORMATION: Quenching domain
<220> FEATURE:
<221> NAME/KEY: MISC_FEATURE
<222> LOCATION: (6)..(18)
<223> OTHER INFORMATION: Linker
<220> FEATURE:

-continued

```
<221> NAME/KEY: MISC_FEATURE
<222> LOCATION: (19)..()
<223> OTHER INFORMATION: PR39

<400> SEQUENCE: 118

Asp Asp Asp Asp Glu Gly Gly Gly Gly Gly Gly Gly Gly Gly Gly
1               5                   10                  15

Gly Glu Arg Arg Arg Pro Arg Pro Pro Tyr Leu Pro Arg Pro Arg Pro
            20                  25                  30

Pro Pro Phe Phe Pro Pro Arg Leu Pro Pro Arg Ile Pro Pro Gly Phe
        35                  40                  45

Pro Pro Arg Phe Pro Pro Arg Phe Pro
50                  55
```

RECOMBINANT PRODUCTION OF ANTIMICROBIAL PEPTIDES

CROSS-REFERENCE TO RELATED APPLICATIONS

This application is a 35 U.S.C. 371 national application of PCT/DK2004/000605 filed Sep. 13, 2004, which claims priority or the benefit under 35 U.S.C. 119 of Danish application no. PA 2003 01310 filed Sep. 11, 2003 and U.S. provisional application No. 60/502,761 filed Sep. 12, 2003, the contents of which are fully incorporated herein by reference.

FIELD OF THE INVENTION

The present invention relates to the field of recombinant production of antimicrobial agents, in particular to co-expression of antimicrobial agents and enzymes, as well as to the use of a protection domain wherein at least 50% of the amino acid residues comprised in the domain are D (asparagin, Asp) and/or E (glutamine, Glu).

BACKGROUND OF THE INVENTION

Background Art

WO 96/14413 discloses various expression vectors used to express recombinant human lactoferrin in various strains of *Aspergillus*. One expression plasmid, for expression in *Aspergillus awamori*, contains the glucoamylase promoter, signal sequence, and sequence encoding 498 amino acids of the endogenous pro-glucoamylase of *Aspergillus awamori*, fused to human lactoferrin. For expression of human lactoferrin in *Aspergillus oryzae*, the expression plasmid incorporates the *Aspergillus oryzae* AMY II gene that encodes the alpha-amylase promoter, secretory signal sequence and first codon of mature alpha-amylase. For expression of human lactoferrin in *Aspergillus nidulans*, the expression plasmid incorporates 300 bp of the 5'-flanking sequence of the *A. nidulans* alcA gene containing all the regulatory elements necessary for controlled gene expression, including the alcohol dehydrogenase promoter from *A. nidulans*.

WO 96/28559 discloses the expression of certain cationic antimicrobial proteins as fusion proteins with an anionic portion for suppressing the anti-microbial activity of the cationic protein. Examples of anionic carrier peptides are glutathione-S-transferase, protein A from *Staphylococcus aureus*, two synthetic IgG-binding domains (ZZ) of protein A, and outer membrane protein F from *Pseudomonas aeruginosa*.

WO 98/54336 discloses the expression of certain antimicrobial proteins as fusion proteins with a negatively charged acidic peptide having at least two cysteine residues.

WO 00/75344 discloses the expression of an exogenous polypeptide as fusions with pectate lyase using various linkers, for example (repeats of) PEPT (SEQ ID NO: 79), EPTP (SEQ ID NO: 80), PTEP (SEQ ID NO: 81), TPEP (SEQ ID NO: 82) or IEGR (SEQ ID NO: 83). Examples of exogenous polypeptides are single chain human insulin, human GLP1, and various alpha-amylases.

Okamoto et al in Plant Cell Physiol. 39(1):57-63 (1998) discloses the expression of the antimicrobial peptide Sarcotoxin IA by GUS fusion in transgenic tobacco plants. GUS designates the protein coding sequence of beta-glucuronidase.

It is an object of the present invention to provide improved methods for production of antimicrobial agents.

SUMMARY OF THE INVENTION

In a first aspect, the invention relates to a recombinant microbial host cell comprising a first nucleic acid sequence encoding an antimicrobial agent, and a second heterologous nucleic acid sequence encoding an enzyme. Either of the nucleic acid sequences, preferably both, may be integrated into the chromosome of the host cell, or they may be present in one or more extrachromosomal entities.

In a second aspect, the invention relates to a nucleic acid construct comprising a first nucleic acid sequence encoding an antimicrobial agent, and a second nucleic acid sequence encoding an enzyme, operably linked to one or more control sequences that direct the expression of the enzyme and the antimicrobial agent in a suitable expression host, wherein the second nucleic acid sequence is heterologous to the expression host.

In a third aspect, the invention relates to a method of producing the enzyme and/or the antimicrobial agent by use of the recombinant host cell of the invention.

In a fourth aspect, the invention relates to fusion products comprising an enzyme, an antimicrobial agent, and a cleavable linker, as well as the use thereof in animal feed and animal feed additives.

In a fifth aspect, the invention relates to the use of co-expression of an antimicrobial peptide and an enzyme as a tool to improve the yield of the peptide and/or to improve overall production economy.

In a sixth aspect, the invention relates to the use, in the recombinant production of an antimicrobial peptide, of a quenching domain serving to temporarily and reversibly inactivate the peptide during its expression, wherein at least 50% of the amino acid residues comprised in the peptide protection domain are D and/or E. The invention also relates to a method of identifying such quenching domains, the quenching domains as identified by the method, and their use in the recombinant production of antimicrobial peptides.

DETAILED DESCRIPTION OF THE INVENTION

Generally, whenever "a" is mentioned herein it means "at least one," for example in the context of the first and second nucleic acid sequences, the antimicrobial agent, the enzyme, and the various DNA constructs.

The present invention relates to the co-expression of at least one enzyme with at least one antimicrobial agent. The enzyme and the antimicrobial agent may be co-expressed from the chromosome of the host cells, from different DNA constructs, from one DNA construct, or using a mixture of these techniques. When using different constructs, different selectable markers, and different origins of replication may be used. When using only one construct, the genes can be expressed from one or more promoters. If cloned under the regulation of one promoter (di- or multi-cistronic), the order in which the genes are cloned may affect the expression levels of the proteins. The enzyme and the antimicrobial agent may also be expressed as a fusion protein, i.e. that the gene encoding the enzyme has been fused in frame to the gene encoding the antimicrobial agent. If the antimicrobial agent would negatively influence the growth of the host cell chosen, the antimicrobial activity can be quenched by expressing the peptide as a fusion with a protection peptide (a quenching domain) wherein at least 50% of the amino acid residues are D and/or E (Asp and/or Glu).

Antimicrobial Agent

In the present context, the term an antimicrobial agent designates a compound with antimicrobial activity (see below). Examples of antimicrobial agents are antimicrobial peptides and antimicrobial enzymes.

Examples of antimicrobial enzymes are enzymes which disrupt the cell wall, generate toxic compounds, remove essential nutrients, or inactivate compounds essential for growth of undesired microorganisms. Lysozyme (an enzyme having 1,4-beta-acetylmuramidase activity) is an example of an antimicrobial enzyme which disrupts the cell wall of gram-positive bacteria. Oxidases, such as glucose oxidase (EC 1.1.3.4), generate hydrogen peroxide which is toxic to many undesired microorganisms. Other examples of antimicrobial enzymes which generate toxic compounds are xanthine oxidase, lactoperoxidase, lipase, myeloperoxidase, and phospholipase. Glucose oxidase is also an example of an enzyme which removes essential nutrients, namely oxygen, thereby preventing growth of aerobic undesired microorganisms. Finally, sulfhydryloxidase is an example of an antimicrobial enzyme which is capable of inactivating essential compounds, viz. those essential enzymes of the undesired microorganism, the activity of which depend on intact sulfhydryl groups. These enzymes are well-known and have been recombinantly produced, see for example for lysozyme and glucose oxidase Bio/Technology 8, 1990, 741-745, and WO 89/12675, respectively.

In a particular embodiment, the antimicrobial enzyme is selected from amongst lysozymes, glucose oxidases, sulphydryl oxidases, peroxidases, and xanthine oxidases, preferably the antimicrobial enzyme is a lysozyme and/or a glucose oxidase.

Turning now to the antimicrobial peptides, in a particular embodiment, the antimicrobial peptides for use according to the invention encompass no more than 100 amino acids.

The expression "encompasses no more than" a certain number of amino acids (e.g. 100) means that the number of amino acids in the peptide sequence is less than or equal to 100.

In particular embodiments, the peptide comprises, or has, or consists of no more than 100 amino acids (and vice-versa for the additional upper limit figures mentioned below).

In further particular embodiments, the peptide encompasses no more than 90, 80, 70, 60, 50, or no more than 40 amino acids.

The peptide may also be designated an oligopeptide.

In another particular embodiment, the peptide encompasses at least 3 amino acids.

The expression "encompasses at least" a certain number of amino acids (e.g. 3) means that the number of amino acids in the peptide sequence is higher than or equal to 3.

In additional particular embodiments, the peptide encompasses at least 4, 5, 6, 7, 8, 9, 10, 11, 12, 13, 14, 15, 16, 17, 18, 19, or at least 20 amino acids.

In still further particular embodiments, the peptide comprises, or has, or consists of at least 3 amino acids (and vice-versa for the additional lower limit figures mentioned above).

Examples of antimicrobial peptides for use according to the invention are listed below.

Antimicrobial Activity

The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect.

The term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., Journal of Immunological Methods, Vol. 137 (2) pp. 167-174 (1991).

Peptides, and/or enzymes, having antimicrobial activity may be capable of reducing the number of living cells of *Escherichia coli* (DSM 1576) to 1/100 after 8 hours (preferably after 4 hours, more preferably after 2 hours, most preferably after 1 hour, and in particular after 30 minutes incubation at 20° C. in an aqueous solution of 25%(w/w); preferably in an aqueous solution of 10%(w/w); more preferably in an aqueous solution of 5%(w/w); even more preferably in an aqueous solution of 1%(w/w); most preferably in an aqueous solution of 0.5%(w/w); and in particular in an aqueous solution of 0.1%(w/w) of the peptides having antimicrobial activity.

Peptides, and/or enzymes, having antimicrobial activity may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

Peptides, and/or enzymes, having antimicrobial activity may be capable of reducing the number of living cells of *Bacillus subtilis* (ATCC 6633) to 1/100 after 30 min. incubation at 20° C. in an aqueous solution of 25%(w/w); preferably in an aqueous solution of 10%(w/w); more preferably in an aqueous solution of 5%(w/w); even more preferably in an aqueous solution of 1%(w/w); most preferably in an aqueous solution of 0.5%(w/w); and in particular in an aqueous solution of 0.1%(w/w) of the peptides having antimicrobial activity.

Peptides, and/or enzymes, having antimicrobial activity may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

A detailed assay for antimicrobial activity is described in Example 1.

In a particular embodiment, as an alternative to the antimicrobial activity, or in addition to the antimicrobial activity, the peptide, and/or the enzyme, has an imunostimulatory effect. This immunostimulatory effect can be mediated through an increase in the oxidative burst in macrophages or alternatively through an increased proliferation of lymphocytes.

Examples of antimicrobial peptides (AMPs) are membrane-active antimicrobial peptides, or antimicrobial peptides affecting/interacting with intracellular targets, e.g. binding to cell DNA. They generally have low hemolytic activity and/or cytotoxicity against normal mammalian cells. Haemolysis is performed on erythrocytes and measured through the release of hemoglobin. Cytotoxicity is performed on relevant cell lines, e.g. human ME180 cervical epithelial cells (ATCC HTB-33) or A549 human lung epithelial cells (ATCC CCL-185) using a tetrazolium reduction assay (Boeringer-Mannheim, Indianapolis, USA).

The antimicrobial peptide for use according to the invention is generally highly cationic and hydrophobic. It typically contains several arginine and lysine residues, and it may not contain a single glutamate or aspartate. It usually contains a large proportion of hydrophobic residues. The peptide generally has an amphiphilic structure, with one surface being highly positive and the other hydrophobic.

The peptide and the encoding nucleotide sequence may be derived from plants, invertebrates, insects, amphibians and mammals, or from microorganisms such as bacteria and fungi.

The antimicrobial peptide may act on cell membranes of target microorganisms, e.g. through non-specific binding to the membrane, usually in a membrane-parallel orientation, interacting only with one face of the bi-layer.

The antimicrobial peptide typically has a structure belonging to one of five major classes: Alpha-helical, cystine-rich (defensin-like), beta-sheet, peptides with an unusual composition of regular amino acids, and peptides containing uncommon and/or modified amino acids. Still further examples are the antifungal peptides (AFP) from *Aspergillus giganteus* and *Aspergillus niger*, for example those disclosed in WO 02/090384.

In particular embodiments, the antimicrobial peptide for use according to the invention is (i) an alpha-helical peptide, (ii) cystine-rich peptide; (iii) a beta-sheet peptide; (iv) a peptide with an unusual composition of regular amino acids; (v) a peptide containing uncommon modified amino acids; and/or (vi) an antifungal peptide.

In another particular embodiment (vii), the alpha-helical peptide is selected from amongst Novispirin, Magainin 1, Magainin 2, Cecropin A, Cecropin B, Cecropin P1, CAP18, Andropin, Clavanin A, Clavanin AK, Styelin D, Styelin C, Buforin II, and the antimicrobial peptides described in WO 02/000839, DK 2004 000800, PCT/DK2004/000399, and/or PCT/DK2004/000400; as well as any variant or fragment thereof which retains antimicrobial activity.

In a further particular embodiment (viii), the cystine-rich peptide is selected from amongst Plectasin, alpha-Defensin, HNP-1 (human neutrophil peptide), HNP-2, HNP-3, beta-Defensin-12, Drosomycin, gamma1-purothionin, Insect defensin A, and/or the antimicrobial peptides described in WO 03/044049; as well as any variant or fragment thereof which retains antimicrobial activity.

In another particular embodiment (ix), the peptide with an unusual composition is selected from amongst Indolicidin, the Pro-Arg-rich peptide PR39, Bactenicin Bac5, Bactericin Bac7, Histatin 5; poly-L-lysine, and/or the antimicrobial peptides described in DK 2003 001324; as well as any variant or fragment thereof which retains antimicrobial activity.

In a still further particular embodiment (x), the peptide with unusual amino acids is selected from amongst Nisin, Gramicidin A, and/or Alamethicin; as well as any variant or fragment thereof which retains antimicrobial activity.

In an additional particular embodiment (xi), the peptide is an antifungal peptide.

In a still further particular embodiment (xii), the expressed peptide is free of any protecting scaffold proteins.

In a particular embodiment (xiii), the peptide has antimicrobial activity and/or an immunostimulatory effect.

In a still further particular embodiment (xiv), the beta-sheet peptide is selected from amongst lactoferrins, lactoferricins (such as Lactoferricin B), Tachyplesin I, and/or Protegrin PG1-5; as well as any variant or fragment thereof which retains antimicrobial activity.

Lactoferrin is a glycoprotein involved in iron binding and delivery in mammals, where it is found in milk and other body fluids. Examples of lactoferrins are human lactoferrin, bovine lactoferrin, porcine lactoferrin, equine lactoferrin, murine lactoferrin, caprine lactoferrin etc. Lactoferrin was described as an antimicrobial agent more than 20 years ago.

The term lactoferricin as used herein designates fragments of lactoferrin having antimicrobial activity and/or an immunostimulatory effect. In a particular embodiment, the lactoferricin for use according to the invention is derived from Bovine lactoferrin (LFB), a protein of 689 amino acids, which has been produced industrially from cheese whey and supplemented to infant formula for a number of years.

A number of examples of lactoferricins for use according to the invention are listed below (a non-exclusive list):

SEQ ID NOs: 1-4 disclosed in EP 474506 are antimicrobial peptides produced by hydrolysis of lactoferrin;

SEQ ID NOs: 5-19, as well as their derivatives having an amide at the carboxy end, disclosed in EP 503939, are antimicrobial peptides based on amino acids 18-28 of Bovine lactoferrin (LFB(18-28));

SEQ ID NOs: 20-31, as well as their derivatives having an amide at the carboxy end, disclosed in EP 510912, are antimicrobial peptides obtainable by hydrolysis from bovine lactoferrin;

SEQ ID NO: 32 disclosed in EP 629213 is another lactoferrin derivative for the manufacture of a medicament for promoting release of leukotriene B4 from polymorphonuclear neutrophils or histamine from mast cells;

SEQ ID NOs: 1-4, SEQ ID NO: 15, SEQ ID NOs: 20-32, and SEQ ID NOs: 33-46 disclosed in U.S. Pat. No. 5,656,591 are additional examples of antimicrobial peptides based on lactoferrin.

SEQ ID NO: 47 is amino acids 1-50 of bovine lactoferrin (LFB(1-50), and lactoferricin B (abbreviated LFcinB, or LFB (17-41)) designates amino acids 17-41 of SEQ ID NO: 47.

SEQ ID NOs: 48-52, viz. LFB(14-31), LFB(17-31), LFB (18-31), LFB(19-31), and LFB(20-31), respectively, are additional lactoferrin fragments disclosed in J. Peptide Sci. 5: 32-45 (1999) by Rekdal et al, who also discloses SEQ ID NOs: 53-55, viz. variants LFB(17-31)17K, LFB(17-31)20F, and LFB(17-31)17K+20F, respectively.

Additional lactoferricins, e.g. SEQ ID NOs. 56-57, viz. LFB(17-30), and LFB(19-37), respectively, are disclosed by Groenink et al in FEMS Microbiology Letters 179 (1999) 217-222.

According to Vogel et al (Biochem. Cell. Biol. 80 (2002): 49-63), a fragment of LFB must contain the six amino acids 20-25 thereof (LFB(20-25), SEQ ID NO: 58) in order to retain any practical level of antimicrobial activity.

A number of variants of LFB(17-31) are disclosed by Stroem et al in J. Peptide Res. 2000, 56, 265-274, viz. 17A, 18A, 19A, 20A, 21A, 22A, 23A, 24A, 25A, 26A, 27A, 28A, 29A, 30A, and 31A.

Additional variants of LFB(17-31) are disclosed by Haug and Svendsen in J. Peptide Sci. 7: 190-196 (2001), viz. 22F, 24F, and 22F+24F.

In particular embodiments, the antimicrobial peptide for use according to the invention (a) comprises SEQ ID NO: 58; (b) comprises SEQ ID NO: 47, and/or a fragment or variant thereof; (c) comprises any one of SEQ ID NOs: 48-52, SEQ ID NOs: 56-57, and/or a fragment or variant thereof.

Enzymes

An enzyme is a polypeptide having enzyme activity. Other protein products of interest for the purposes of the present invention (co-expression with antimicrobial agents) are hormones, blood clotting factors, immunoglobulins, as well as fragments or variants thereof.

The following is a non-limiting list of examples of enzymes of particular interest: Endoglucanase, xylanase, phytase, protease, galactanase, mannanase, dextranase, and alpha-galactosidase. Additional enzymes of particular relevance are pectate lyase, alpha-amylase and AMG. In a particular embodiment, the enzyme is a xylanase, a phytase, a galactanase, or a protease. In a still further particular embodiment, the enzyme is a phytase, or a protease. In a still further particular embodiment the enzyme is not glutathione-S-transferase. In another particular embodiment the enzyme is not beta-glucuronidase.

There are no limitations on the origin of the enzyme. Thus, the term includes not only natural or wild-type enzymes obtained from microorganisms of any genus, but also any an analogues, mutants, variants, fragments etc. thereof, as well as synthetic enzymes, such as shuffled enzymes, and consensus enzymes, as long as they exhibit the relevant enzyme activity. Such genetically engineered enzymes can be prepared as is generally known in the art, eg by Site-directed Mutagenesis, by PCR, or by Random Mutagenesis.

In a particular embodiment, the enzyme, and/or the nucleotide sequence encoding it, is a heterologous, or exogenous, enzyme and/or nucleotide sequence, respectively. This means that it is foreign to the selected or intended expression host cell. The term heterologous excludes natural or wild-type nucleic acid sequences endogenous to the host cell in question.

In a specific embodiment, the enzyme is a low-allergenic variant, designed to invoke a reduced immunological response when exposed to animals, including man. Low-allergenic variants may be prepared using techniques known in the art.

Enzymes can be classified on the basis of the handbook Enzyme Nomenclature (from NC-IUBMB, 1992), see also the ENZYME site on the World Wide Web (www.expasy.ch/enzyme). ENZYME is a repository of information relative to the nomenclature of enzymes. It is primarily based on the recommendations of the Nomenclature Committee of the International Union of Biochemistry and Molecular Biology (IUB-MB) and it describes each type of characterized enzyme fro which an EC (Enzyme Commission) number has been provided (Bairoch A. The ENZYME database, 2000, Nucleic Acids Res 28:304-305). The IUB-MB Enzyme nomenclature is based on their substrate specificity and occasionally on their molecular mechanism; such a classification does not reflect the structural features of these enzymes.

For the present purposes a xylanase is an enzyme classified as EC 3.2.1.8. The xylanase may be derived from a bacterial xylanase, e.g. from a strain of *Bacillus*, or it may be a fungal xylanases including yeast and filamentous fungal xylanases. Fungal xylanases can, e.g., be derived from a strain of *Aspergillus, Humicola, Thermomyces,* or *Trichoderma.*

For the present purposes, the term endoglucanase designates any enzyme which is classified or can be classified as EC 3.2.1.4, EC 3.2.1.6, EC 3.2.1.73, or EC 3.2.1.39. In particular embodiments, the endoglucanase is an enzyme classified as EC 3.2.1.4 or EC 3.2.1.6. Endoglucanases may be derived from various fungal and bacterial strains, e.g. from strains of *Thermoascus.*

The term protease as used herein is an enzyme that can be classified in the EC 3.4 enzyme group. Examples of proteases are *Aspergillus aculeatus* protease I or protease II; *Aspergillus niger* acid proteinase (protease A)); *Aspergillus oryzae* aspergillopepsin O; the acid-stable subtilisin proteases disclosed at p. 5, lines 19-23 of WO 01/58275 derived from *Bacillus* sp., *Bacillus alcalophilus; Fusarium oxysporum; Paecilomyces lilacinus, Aspergillus* sp., *Acremonium chrysogenum,* and *Acremonium kiliense*; and the acid-stable proteases disclosed in WO 01/58276 at p. 4, line 27-28 derived from *Nocardiopsis* sp. and *Nocardiopsis alba.*

The *Nocardiopsis* sp. protease comprises the amino acid sequence of the mature part (amino acids 1-188) of SEQ ID NO: 59. A preferred protease is A87T of SEQ ID NO: 59, viz. a variant of the protease having amino acids 1-188 of SEQ ID NO: 59 in which Ala in position 87 is substituted with Thr.

Other preferred proteases are the following:

The protease derived from *Nocardiopsis dassonvillei* subsp. *dassonvillei* and comprising the amino acid sequence of the mature part (amino acids 1-188) of SEQ ID NO: 60.

The protease derived from *Nocardiopsis alba* and comprising the amino acid sequence of the mature part (amino acids 1-188) of SEQ ID NO: 61.

The protease derived from *Nocardiopsis prasina* and comprising the amino acid sequence of the mature part (amino acids 1-188) of SEQ ID NO: 62.

A protease derived from *Nocardiopsis prasina* and comprising the amino acid sequence of the mature part (amino acids 1-188) of SEQ ID NO: 63.

In a particular embodiment, the proteases of SEQ ID NO: 59, 60, 61, 62 or 63 are variants comprising an extension, such as an N- or C-terminal extension, preferably a C-terminal extension. The extension may comprise at least three non-polar or uncharged polar amino acids within the last four amino acids of the C-terminus of the polypeptide, in particular these variants have an extension of one or more amino-acid(s) added to the C-terminus as compared to the wildtypes. In further particular embodiments:

i) the one or more added amino acid(s) is (are) non-polar or uncharged;

ii) the one or more added amino acid(s) is one or more of Q, S, V, A, or P;

iii) the one or more added amino acids are selected from the group consisting of: QSHVQSAP (SEQ ID NO: 84), QSAP (SEQ ID NO: 85), QP, TL, TT, QL, TP, LP, TI, IQ, QP, PI, LT, TQ, IT, QQ, and PQ.

In a still further embodiment, the protease has a degree of identity to amino acids 1-188 of SEQ ID NO: 59 of at least 70%, preferably at least 75%, 80%, 85%, 90%, or at least 95%.

For purposes of the present invention the degree of identity between two amino acid sequences is determined by the program "align" which is a Needleman-Wunsch alignment (i.e. a global alignment). The default scoring matrix BLOSUM50 is used for polypeptide alignments. The penalty for the first residue of a gap is −12 for polypeptides, and the penalty for further residues of a gap is −2 for polypeptides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

In the present context a phytase is an enzyme which can be classified as EC 3.1.3.8, and/or EC 3.1.3.26. Phytases may be obtained from, e.g., various strains of *Aspergillus* and *Emericella*, *Thermomyces*, *Humicola*, *Peniophora*, *Penicillium*, *Bacillus*, *Escherichia coli*; or *Schwanniomyces*.

A preferred phytase derives from *Peniophora lycii* and comprises amino acids 1-409 of SEQ ID NO: 64, or is a variant thereof. In a particular embodiment, the variant is selected from the variants disclosed in Tables 1-5 of WO 03/066847.

In a still further particular embodiment, the phytase has a degree of identity to amino acids 31-439 of SEQ ID NO: 64 of at least 75%.

The term galactanase as used herein is an enzyme that can be classified as EC 3.2.1.89. Galactanases may be derived from, e.g., strains of *Aspergillus, Bacillus, Thermotoga, Meripilus, Myceliophthora, Humicola, Pseudomonas, Xanthomonas*, or *Yersinia*.

The term mannanase as used herein means an enzyme which can be classified as EC 3.2.1.78. The mannanase may, e.g., be derived from strains of *Aspergillus, Bacillus*, or *Trichoderma*.

The term dextranase as used herein means an enzyme which can be classified as EC 3.2.1.11. The dextranase may, e.g., be derived from a strain of *Paecilomyces*.

The term alpha-galactosidase as used herein means an enzyme that can be classified as EC 3.2.1.22. The alpha-galactosidase may, e.g., be derived from a strain of *Aspergillus*.

The term alpha-amylase as used herein is an enzyme that can be classified as EC 3.2.1.1.

The term glucoamylase as used herein is an enzyme that can be classified as EC 3.2.1.3.

The term pectate lyase as used herein is an enzyme that can be classified as EC 4.2.2.2.

Strains of the species mentioned above and other strains mentioned herein are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

Nucleic Acid Sequences

The nucleic acid sequences for use in the present invention may be of genomic, cDNA, RNA, semisynthetic, synthetic origin, or any combinations thereof.

The techniques used to isolate or clone a nucleic acid sequence encoding an antimicrobial agent or an enzyme are known in the art and include isolation from genomic DNA, preparation from cDNA, chemical synthesis, or a combination thereof. Most of the peptide genes are synthesized chemically. Peptide genes found by signal trapping (e.g. TAST, i.e. Transposon Assisted Signal Trapping) is of natural origin.

The cloning of the nucleic acid sequences from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used.

The nucleic acid sequence encoding the enzyme and/or the antimicrobial agent may, e.g., be cloned from a strain of the desired bacterium or fungus, or another or related organism and thus, for example, may be an allelic or species variant.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the antimicrobial agent or the enzyme, insertion of the fragment into a vector molecule, and incorporation of the recombinant vector into a host cell where multiple copies or clones of the nucleic acid sequence will be replicated.

Modification of a nucleic acid sequence encoding an antimicrobial agent or an enzyme as defined in claim 1 may be necessary for the synthesis of variant agents or variant enzymes. The terms "variant agent" and "variant enzyme" refer to non-naturally occurring forms of thereof. These may differ in some engineered way from the antimicrobial agent or enzyme as isolated from its native source, e.g., agent or enzyme variants that differ in specific activity, thermostability, pH optimum, allergen city, or agent variants that differ in antimicrobial activity or specificity profile, or the like. The variant sequence may be constructed on the basis of the nucleic acid sequences encoding the agent or the mature part of the enzyme, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme and agent, or by introduction of nucleotide substitutions which may give rise to a different amino acid sequence. For a general description of nucleotide substitution, see, e.g., Ford et al., 1991, Protein Expression and Purification 2: 95-107. Low-allergenic enzymes and antimicrobial agents can e.g. be prepared as described above.

It will be apparent to those skilled in the art that such substitutions can be made outside the regions critical to the function of the molecule and still result in an active agent or enzyme. Amino acid residues essential to the activity of the enzyme or antimicrobial agent encoded by the nucleic acid sequence, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

Nucleic Acid Constructs

The present invention relates to nucleic acid constructs of a certain type, viz. constructs that comprise a first nucleic acid sequence encoding an antimicrobial agent, and a second nucleic acid sequence encoding an enzyme, operably linked to one or more control sequences that direct the expression of these coding sequences in a suitable host cell under conditions compatible with the control sequences. In a particular embodiment, the second nucleic acid sequence is heterologous to the expression host.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression.

The term "a nucleic acid sequence encoding" or "coding sequence" is defined herein as a nucleic acid sequence that directly specifies the amino acid sequence of its peptide or enzyme product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

Expression will be understood to include any step involved in the production of the enzyme and the antimicrobial agent including, but not limited to, transcription, post-transcriptional modification, translation, post-translational modification, and secretion.

The term "control sequences" is defined herein to include all components that are necessary or advantageous for the expression of an enzyme, and an antimicrobial agent, respectively. Each control sequence may be native or foreign to the respective encoding nucleic acid sequence. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences that mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

Preferred terminators for bacterial host cells, such as a *Bacillus* host cell, are the terminators from *Bacillus licheniformis* alpha-amylase gene (amyL), the *Bacillus stearothermophilus* maltogenic amylase gene (amyM), or the *Bacillus amyloliquefaciens* alpha-amylase gene (amyQ).

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevi-* siae alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of an enzyme and directs the encoded enzyme into the cell's secretory pathway. The 5' end of the coding sequence of the nucleic acid sequence may inherently contain a signal peptide coding region naturally linked in translation reading frame with the segment of the coding region which encodes the secreted enzyme. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the enzyme. However, any signal peptide coding region which directs the expressed enzyme into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* betalactamase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of an enzyme. The resultant enzyme is known as a proenzyme or propolypeptide (or a zymogen in some cases). A proenzyme is generally inactive and can be converted to a mature active enzyme by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of an enzyme, the propeptide region is positioned next to the amino terminus of an enzyme and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the enzyme would be operably linked with the regulatory sequence.

The nucleic acid construct of the invention may comprise more than one nucleic acid sequence encoding more than one enzyme, e.g. one, two, three, four, five, six, seven, eight, nine or ten nucleic acid sequences encoding one, two, three, four, five, six, seven, eight, nine or ten enzymes. The enzymes may be the same or different. The nucleic acid sequences encoding the enzyme(s) may be the same or different.

The nucleic acid construct of the invention may also comprise more than one nucleic acid sequence encoding more than one antimicrobial agent, e.g. one, two, three, four, five, six, seven, eight, nine, ten, eleven, twelve, thirteen, fourteen, fifteen, sixteen, seventeen, eighteen, nineteen, or twenty nucleic acid sequences encoding one, two, three, four, five, six, seven, eight, nine, ten, eleven, twelve, thirteen, fourteen, fifteen, sixteen, seventeen, eighteen, nineteen, or twenty antimicrobial agents. The nucleic acid construct of the invention may also comprise more than twenty nucleic acid sequences encoding more than twenty antimicrobial agents, e.g. up to twenty-five, thirty, thirty-five, fourty, fourty-five, or even up to fifty nucleic acid sequences encoding up to twenty-five, thirty, thirty-five, fourty, fourty-five, or even up to fifty antimicrobial agents. The antimicrobial agents may be the same or different. The nucleic acid sequences encoding the antimicrobial agent(s) may be the same or different. The numbers of nucleic acid sequences may in particular be in the higher range when expression takes place in inclusion bodies.

In the nucleic acid construct of the invention, the nucleic acid sequence(s) encoding the enzyme(s) may be upstream of the nucleic acid sequence(s) encoding the antimicrobial agent(s), or vice versa. Still further, some of the enzyme encoding sequences may be upstream, some downstream, of the antimicrobial agent encoding sequences, and vice versa.

Of course, as is common general knowledge, in all nucleic acid constructs described herein the individual component sequences, such as the nucleic acid sequences encoding the enzyme(s), the antimicrobial agent(s), the control sequences, and also the linkers and domains described further below, should be properly spaced and juxtaposed so as to enable the desired, correct, expression to occur.

Three examples a)-c) of relatively simple nucleic acid constructs of the invention are listed below. The constructs are listed in the usual direction of 5' to 3', and the following abbreviations are used: AMP: Anti Microbial Peptide; ENZ: Enzyme; RBS: Ribosome Binding Site, PROM: Promoter; TERM: Terminator):

a) PROM-RBS1-Gene(AMP)-Linker-Gene(ENZ)-TERM
b) PROM-RBS1-Gene(AMP)-RBS2-Gene(ENZ)-TERM
c) PROM1-RBS1-Gene(AMP)-TERM1-PROM2-RBS2-Gene(Enzyme)-TERM2

Ad a): This construct results in one transcriptional product, and one translational product, viz. a fusion protein (fusion product). In the above constructs, "Linker" designates a cleavable linker, which is described in more detail below, and which provides for subsequent cleavage of the fusion protein, AMP-Linker-ENZ, into distinct products, AMP, and ENZ, respectively.

Ad b): This construct results in one transcriptional product, but two translational products, as the translation will stop because of the translational stop codon inherent in Gene (AMP). Accordingly, two distinct products, AMP and ENZ, will be produced.

Ad c): In this construct, transcription will stop after Gene (AMP), but the transcription continues at PROM2. Accordingly, two transcription products, as well as two translational products, AMP and ENZ, result from this construct. By applying PROM1 and PROM2 promoters of varying strength, or by using one or more inducible promoters, the expression of AMP can be regulated as compared to ENZ, or vice versa, e.g with a view to obtain desired molar ratios of expressed AMP versus ENZ.

The below constructs d)-f) are non-limiting examples of nucleic acid constructs of the invention incorporating more than one nucleic acid sequence encoding the enzyme and/or the peptide. The same notation as above applies, the control sequences, linkers etc. are however excluded for the sake of simplicity:

d) Gene(ENZ)-Gene(AMP)-Gene(AMP)
e) Gene(ENZ)-Gene(AMP)-Gene(AMP)-Gene(AMP)
f) Gene(ENZ)-Gene(AMP)-Gene(AMP)-Gene(AMP)-Gene(ENZ)

In the above constructs, AMP can designate the same or different AMP sequences, and the same holds true for ENZ.

Cleavable Linkers

At the amino acid level, the term "cleavable linker" is defined herein as a sequence of amino acids, typically relatively short, e.g. consisting of 1-30 amino acids which comprises a cleavage site. The term "cleavage site" means a specific sequence of amino acids, typically very short, e.g. consisting of 1-10 amino acids which can be cleaved specifically by a cleavage agent, viz. by physical or chemical, typically enzymatical, means. Non-limiting examples of cleavable linkers, recognition and cleavage sites, and cleavage agents are listed below.

For example, the cleavable linker can be a recognition site for a site-specific protease. An example of a site-specific protease (cleavage agent) is the Kex2 membrane bound proteinase from alpha-cells of the yeast *Saccharomyces cerevisiae*. The Kex2 proteinase hydrolyzes peptides and proteins with basic amino acid pairs which are cleaved at the C-ends of their peptide bonds (Bessmertnaya et al. (1997) Biochemistry, Vol. 62 (8) pp. 850-857. Examples of Kex2 cleavage sites are Lys-Arg (K-/-R) and Arg-Arg (R-/-R), and also other combinations of basic amino acids could be inserted to optimize the cleavage by Kex2 (Ledgerwood. et al. (1995) J. Biochem., Vol. 308 (1) pp. 321-325; or Ghosh, S. et al. (1996) Gene (Amsterdam), Vol. 176 (1-2) pp. 249-255).

Other useful combinations of proteases (cleavage agents) and cleavage linkers are: Enterokinase (LaVallie et al. (1993) J. Biol. Chem., Vol 268 pp. 2311-2317) with a preference for cleaving the amino acid sequence X-D-D-D-K-/-X (SEQ ID NO: 86), Trypsin (Jonasson et al. (1996) Eur. J. Biochem., Vol 236 (2) pp. 656-661) with a preference for cleaving the amino acid sequence X-K-R-/-X (SEQ ID NO: 87), Factor Xa (Nagai et al. (1985) PNAS, Vol 82 pp. 7252-7255) with a preference for cleaving the amino acid sequence X-I-E-G-R-/-X (SEQ ID NO: 88), Collagenase (Chinery et al. (1993) Eur. J. Biochem., Vol 212 (2) pp. 557-553) with a preference for cleaving the amino acid sequence P-X-/-G-P-X-X (SEQ ID NO: 89), Thrombin (Rahman et al. (1992) Cell. Mol. Biol., Vol 38 (5) pp. 529-542) with a preference for cleaving the amino acid sequence X-G-V-R-G-P-R-/-X (SEQ ID NO: 90), ALP (*Achromobacter lyticus* Lys-specific protease) (Kjeldsen et al., (1996) Gene, Vol 170 (1) pp. 107-112) with a preference for cleaving at Lysine, and the C-component protease from *Bacillus licheniformis* cleaving at Glu (Kakudo et al. (1992) J. Biol. Chem., Vol 267 (33) pp. 23782-23788). Digestive proteases are additional useful proteases, in particular trypsin (mentioned above), but also pepsin, chymotrypsin, and pancreas protease. Chymotrypsin may have a preference for cleaving after aromatic amino acids and Leu.

Another preferred method of cleaving a peptide at a specific target site is by using chemical compounds such as cyanogen-bromide which cleaves X-M-/-X or hydroxylamine which cleaves S-N-/-G-X (SEQ ID NO: 91) (Current protocols in Molecular Biology. John Wiley and Sons, 1995; Harwood, C. R., and Cutting, S. M. (eds.)).

A still further specific cleavage method is available for D-/-P (Asp-Pro) peptide bonds, which can be cleaved by treatment with a weak acid (e.g. pH 2-3) at a suitable temperature, for a suitable time period. Examples of suitable temperatures are 40, 50, 60, 70, or 80° C., and examples of suitable time periods are from a few minutes to a few hours, e.g. ¼ hour to 5 hours, ½ hour to 2½ hours, 1 hour to 3 hours, 1½ hours to 2½ hours.

At nucleotide level, nucleotide sequences corresponding to the above cleavage linkers, as well as to the below peptide protection domains, are of course easily deduced by the person skilled in the art by reference to the genetic code. The nucleotide sequences can also be optimized for the codon usage of the host cell in question, as is well known in the art.

Protection Peptides

The present invention also relates to the use, in the recombinant expression of antimicrobial peptides, of a so-called quenching domain, or protection peptide, or protection domain, which is characterized in that at least 50% of its component amino acid residues are E and/or D. The purpose of such protection domain is to temporarily inactivate the antimicrobial peptide, in case it would be inhibiting the growth of the host cell. Once sufficient quantities of the peptide have been produced, the protection peptide can be cleaved off as described further below, thus re-activating the antimicrobial peptide. The protection peptide is preferably synthetic (artificial).

In particular embodiments, at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or at least 99% of the amino acid residues comprised in the protection peptide are D and/or E. In a further particular embodiment, the complete amino acid sequence of the protection peptide consists of the amino acid residues D and/or E. In a still further particular embodiment, the protection peptide consists of at least one of the amino acid residues D and/or E, and, optionally, a cleavage linker.

In particular, or alternative, embodiments of this aspect of the invention: (1) The number of D and/or E amino acid residues in the protection peptide is higher than the number of R and/or K residues; (2) the protection peptide does not contain any C residues; (3) the number of amino acid residues in the protection peptide is lower than the number of amino acid residues in the antimicrobial peptide; and/or (4) the protection peptide is not an inhibitor of bacterial proteases.

In a particular embodiment, the protection peptide designates that part of the expressed fusion product which is not the antimicrobial agent, and which is not the signal peptide part, if any. In other particular embodiments, the protection peptide is a stretch of amino acids close to the antimicrobial peptide. The length of the protection peptide is described in more detail below. The protection peptide and the antimicrobial peptide may be separated by a stretch of amino acids of up to 5, up to 8, up to 10, up to 12, up to 15, up to 20, up to 25, or up to 30 amino acids.

The nucleic acid sequence encoding the peptide protection domain may be upstream or downstream of the antimicrobial peptide encoding nucleic acid sequence. In further aspects hereof, the invention relates to a nucleic acid construct comprising a first nucleic acid sequence encoding an antimicrobial peptide, and a second nucleic acid sequence encoding a peptide protection domain as defined above; as well as a recombinant host cell comprising such construct; and a method for production of the antimicrobial peptide by cultivation of the recombinant host cell, and recovery of the peptide, the method optionally comprising the step of cleaving the peptide protection domain using an appropriate cleavage agent, examples of which are mentioned above.

In particular embodiments of these quenching aspects of the invention, everything what is stated herein in relation to the co-expression aspects of the invention also applies to the quenching aspect. This is so in particular, e.g., in relation to the antimicrobial peptide, the control sequences, the host cells etc. Likewise, everything what is stated herein in relation to the quenching aspects is applicable to the co-expression aspects of the invention.

The protection peptide is typically an oligopeptide or a peptide comprising a number of natural, non-natural or modified amino acids that are linked by peptide bonds. In a particular embodiment the constituent amino acids are natural L-amino acids.

Typically, the protection peptide encompasses, in the alternative consists of, between 1 and 100, 1 and 95, 1 and 90, 1 and 85, 1 and 80, 1 and 75, 1 and 70, 1 and 65, 1 and 60, 1 and 55, 1 and 50, 1 and 45, 1 and 40, 1 and 35, 1 and 30, 1 and 25, 1 and 20, 1 and 15, or between 1 and 10 amino acid residues.

In further particular embodiments, the protection peptide encompasses, in the alternative consists of, between 1 and 100, 2 and 100, 3 and 100, 4 and 100, 5 and 100, 6 and 100, 7 and 100, 8 and 100, 9 and 100, or 10 and 100 amino acid residues.

In additional particular embodiments, the protection peptide encompasses, in the alternative consists of, between 1 and 100, 2 and 90, 3 and 80, 4 and 70, 5 and 60, 5 and 50, 5 and 40, 5 and 35, 5 and 30, 5 and 25, or between 5 and 20 amino acid residues.

These are non-limiting examples of protection peptides of the invention (in the conventional direction, N-terminal first): E, D, ED, DE, DDE, EED, DED, EDE, DDEEE (SEQ ID NO: 92), DDDEE (SEQ ID NO: 93), DDDDE (SEQ ID NO: 94), EEDDE (SEQ ID NO: 95), DDEED (SEQ ID NO: 96), EDEDE (SEQ ID NO: 97), DDDEEE (SEQ ID NO: 98), DEDEDE (SEQ ID NO: 99), and EEDDEE (SEQ ID NO: 100).

In a particular embodiment, the protection peptide is selected from amongst the following: DP, DDDDDP (SEQ ID NO: 101), EEEEEDP (SEQ ID NO: 102), E, DE, DDE, DDDE (SEQ ID NO: 103), DDDDE (SEQ ID NO: 94), DEDEDEDP (SEQ ID NO: 104), DDDGGEEEGGDDDP (SEQ ID NO: 105), and DDDGGDDDPPDDDE (SEQ ID NO: 106).

Those of the above protection peptides which contain E are by the way also cleavable linkers per se, because e.g. the C-component protease from *Bacillus licheniformis* will cleave at the carboxy-terminal side of the E.

Those of the above protection peptides which encompass DP are cleavable by weak acids, see above.

In the alternative, or in addition, these protection peptides can be combined with any suitable cleavage linker to enable their post-productional separation from the antimicrobial peptide.

The table below shows for selected examples of protection peptides how to calculate the percentage of D and/or E residues.

| Protection Peptide | Number of amino acids | Number of D/E residues | Percentage of D/E residues |
|---|---|---|---|
| DP | 2 | 1 | 50 |
| DDDDDP (SEQ ID NO: 101) | 6 | 5 | 83 |
| EEEEEDP (SEQ ID NO: 102) | 7 | 6 | 86 |
| DDDDE (SEQ ID NO: 94) | 5 | 5 | 100 |
| DEDEDEDP (SEQ ID NO: 104) | 8 | 7 | 88 |
| DDDGGEEEGGDDDP (SEQ ID NO: 105) | 14 | 9 | 64 |
| DDDGGDDDPPDDDE (SEQ ID NO: 106) | 14 | 10 | 71 |

The protection peptides of the invention may be identified by a) providing a peptide protection candidate comprising at least one D and/or E; b) preparing a DNA construct comprising a first DNA sequence encoding the peptide protection candidate and a second DNA sequence encoding an antimicrobial peptide; c) transforming a host cell with the DNA construct of b) and cultivating the transformed host cell to obtain expression of the DNA construct; d) estimating viability of the transformed host cell and/or yield of antimicrobial peptide; and e) identifying a peptide protection candidate which when used in a DNA construct according to step b), for transformation of a host cell according to step c), results in an increased viability of the host cell, and/or an increased yield of antimicrobial peptide, when estimated according to step d).

The viability of the transformed host cell may be measured as is well-known in the art, e.g. by measuring optical density (OD) at 450 or 600 nm, for example at 450 nm. The yield of the antimicrobial agent, for example the antimicrobial peptide, may be estimated on a coomassie-stained SDS gel, e.g. by looking for bands of the expected molecular weight and, if desired, also band intensity (see Example 5).

Expression Vectors

The present invention also relates to recombinant expression vectors comprising a first nucleic acid sequence encoding an antimicrobial agent; a second nucleic acid sequence encoding an enzyme; a promoter; and transcriptional and translational stop signals.

The various nucleic acid and control sequences described above may be joined together to produce a recombinant expression vector which may include one or more convenient restriction sites to allow for insertion or substitution of the nucleic acid sequences encoding the enzyme and the antimicrobial agent at such sites. Alternatively, the nucleic acid sequences of the present invention may be expressed by inserting the nucleic acid sequences or a nucleic acid construct comprising the sequences into an appropriate vector for expression. In creating the expression vector, the coding sequences are located in the vector so that the coding sequences are operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cells include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the enzyme, or the nucleic acid sequence encoding the antimicrobial agent, or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proceedings of the National Academy of Sciences USA 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention relates to recombinant host cells comprising a first nucleic acid sequence encoding an antimicrobial agent, and a second heterologous nucleic acid sequence encoding an enzyme.

These host cells are advantageously used in the recombinant production of the antimicrobial agent and the enzyme. At least one vector comprising the corresponding nucleic acid sequences is introduced into a host cell, so that the vector(s) is maintained as a chromosomal integrant or as a self-replicating extra-chromosomal vector as described earlier. The term "host cell" encompasses any progeny of a parent cell that is not identical to the parent cell due to mutations that occur during replication. Generally, the choice of a host cell will to a large extent depend upon the gene encoding the antimicrobial agent, and/or on the gene encoding the enzyme and its source. For example, a host cell may be selected which is not affected, or affected to a very limited extent only, by the antimicrobial activity of the agent. In the alternative, the host cell is protected from the antimicrobial activity by provisionally or temporarily inactivating (quenching) the peptide. Still further, generally, a fungal enzyme is preferably expressed in a fungal host cell, and a bacterial enzyme in a bacterial host cell.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may be a eukaryote, such as a non-human animal cell, an insect cell, a plant cell, or a fungal cell.

In one particular embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another particular embodiment, the fungal host cell is a yeast cell. "Yeast" as used herein includes *ascosporogenous* yeast (*Endomycetales*), *basidiosporogenous* yeast, and yeast belonging to the Fungi *Imperfecti* (*Blastomycetes*). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium, Series No. 9, 1980).

The yeast host cell may be a *Candida, Hansenula, Kluyveromyces, Pichia, Saccharomyces, Schizosaccharomyces*, or *Yarrowia* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Examples of filamentous fungal host cells are cells of species of, but not limited to, *Acremonium, Aspergillus, Fusarium, Humicola, Mucor, Myceliophthora, Neurospora, Penicillium, Thielavia, Tolypocladium*, or *Trichoderma*.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

In a particular embodiment the host cell is a microbial host cell, which includes bacterial host cells and fungal host cells, as defined above.

Methods of Production

The present invention also relates to methods for producing an enzyme and an antimicrobial agent, the method comprising (a) cultivating a host cell of the invention under conditions conducive for production of the enzyme and the antimicrobial agent; and (b) recovering the enzyme and/or the antimicrobial agent.

In the production methods of the present invention, the cells are cultivated in a nutrient medium suitable for production of the enzyme and the antimicrobial agent using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

If the enzyme and the antimicrobial agent are secreted into the nutrient medium, they can be recovered directly from the medium. If they are not secreted, they can be recovered from cell lysates.

The enzyme may be detected using methods known in the art that are specific for the enzyme in question. These detection methods may include use of specific antibodies, formation of an enzyme-product, or disappearance of an enzyme-substrate. For example, an enzyme assay may be used to determine the activity of the enzyme as described herein. The antimicrobial agent may be detected using antibodies directed against one or more epitopes on the peptide, or the peptide may be detected using antimicrobial activity.

The following are examples of products commonly referred to above as "the enzyme and the peptide":

a) A fusion product, which briefly may be designated AMP-ENZ, however, as explained above the order of AMP and ENZ can be reversed, and the number and kind of individual AMP and ENZ entities can vary;

b) AMP and ENZ as separate entities (varying numbers, varying kinds as explained above);

c) AMP-Q and ENZ as separate entities, the expression AMP-Q designating the attachment of a protective (Quenching) domain to the AMP molecule (again, varying numbers, varying kinds, as explained above); and d) A fusion product AMP-Q-ENZ (varying numbers, kinds, relative position etc. as explained above).

As desired, only the enzyme may be recovered, only the antimicrobial agent may be recovered, or both products may be recovered.

These products may be recovered by methods known in the art. For example, they may be recovered by conventional procedures including, but not limited to, centrifugation, filtration, extraction, spray-drying, evaporation, or precipitation.

The products may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. C. Janson and Lars Ryden, editors, VCH Publishers, New York, 1989).

When the enzyme and the antimicrobial agent are expressed as two distinct products, they may be separated, e.g. by gel filtration, and the further purification of one or both of these products, if desired or required, may then follow conventional routes as described above.

In a particular embodiment of the method for producing the enzyme and the antimicrobial agent, the method comprises a step of cleaving the fusion product, i.e. separating the antimicrobial agent and enzyme parts of the fusion product. This can be done using appropriate cleavage agents, examples of which are described above. The cleavage step can be performed before, during or after the recovery procedure, or the cleavage can be done at any time after the recovery, e.g. by an end-user or by a purchaser of the fusion product, e.g. just prior to the intended end-use of the product, or as a step in a procedure of preparing an intermediate product, e.g. an animal feed additive.

In another embodiment, in connection with the use of the fusion product in animal feed, the fusion product is not cleaved at all before intake by the animal, but digestive proteases and/or chemical/physical conditions in the digestive system of the animal in question takes care of the cleavage, and the active enzyme and antimicrobial agent molecules are accordingly only released in vivo, upon digestion by an animal. Digestive proteases are examples of appropriate cleavage agents for such embodiment.

In a still further embodiment of the method of the invention, the protection peptide, or a part thereof, is separated from the antimicrobial peptide part in a cleavage step, that may be the same as the cleavage step described above, or an a separate, additional cleavage step.

A further particular embodiment of the method of the invention comprises the step of adding additional enzyme and/or antimicrobial agent molecules to the product resulting from the recovery procedure. This could be with a view to obtaining a product with a desired molar ratio between the antimicrobial agent(s) and the enzyme(s).

Plants

The present invention also relates to a transgenic plant, plant part, or plant cell which has been transformed with nucleic acid sequences encoding an enzyme and an antimicrobial agent so as to express and produce these in recoverable quantities. The enzyme and the antimicrobial agent may be recovered from the plant or plant part. Alternatively, the plant or plant part containing these products may be used as such for improving the quality of a food or feed, e.g., improving nutritional value, palatability, and rheological properties, or to destroy an antinutritive factor.

In a particular embodiment, the enzyme and the antimicrobial agent are targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, Poa), forage grass such as festuca, lolium, temperate grass, such as Agrostis, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689, 054 and U.S. Pat. No. 6,111,168 are examples of engineered plants.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing an antimicrobial agent and an enzyme of the present invention may be constructed in accordance with methods known in the art. Briefly, the plant or plant cell is constructed by incorporating one or more expression constructs encoding the enzyme and the antimicrobial agent into the plant host genome and propagating the resulting modified plant or plant cell into a transgenic plant or plant cell.

Conveniently, the expression construct is a nucleic acid construct which comprises a nucleic acid sequence encoding the enzyme and a nucleic acid sequence encoding the antimicrobial agent, operably linked with appropriate regulatory sequences required for expression thereof in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the antimicrobial agent and the enzyme are desired to be expressed. For instance, the expression of the genes may be constitutive or inducible, or may be developmental, stage or tissue specific, and the gene products may be targeted to a specific tissue or plant part such as seeds or leaves. Regulatory sequences are, for example, described by Tague et al., 1988, Plant Physiology 86: 506.

For constitutive expression, the 35S-CaMV promoter may be used (Franck et al., 1980, Cell 21: 285-294). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588).

A promoter enhancer element may also be used to achieve higher expression of the enzyme and the antimicrobial agent in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art.

The present invention also relates to methods for producing an enzyme and an antimicrobial agent, the method comprising (a) cultivating a transgenic plant or a plant cell comprising the encoding nucleic acid sequences under conditions conducive for production of the antimicrobial agent and the enzyme; and (b) recovering these.

Animals

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with nucleic acid sequences encoding an enzyme and an antimicrobial agent so as to express and produce these. The agent and the enzyme may be recovered from the animal, e.g. from the milk of female animals, or they may be expressed to the benefit of the animal itself, e.g. to assist the animal's digestion. Examples of animals are mentioned below in the section headed Animal Feed.

To produce a transgenic animal with a view to recovering the antimicrobial agent and the enzyme from the milk of the animal, the encoding nucleic acid sequences may be inserted into the fertilized eggs of an animal in question, e.g. by use of transgene expression vector(s) which comprises a suitable milk protein promoter, and the desired nucleic acid sequences. The transgene expression vector is is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The enzyme and the agent may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including transgenes encoding the antimicrobial agent and the enzyme, the transgene may be operably linked to a first regulatory sequence for salivary gland specific expression, as disclosed in WO 00/064247.

Compositions

In a still further aspect, the present invention relates to compositions comprising the fusion product of antimicrobial agent and enzyme, if desired with a protection peptide (such as AMP-(Q)-ENZ), as described above.

These compositions may be prepared in accordance with methods known in the art and may be in the form of a liquid or a dry composition. For instance, they may be in the form of granulates or microgranulates. The enzyme and the antimicrobial agent to be included in the composition may be stabilized in accordance with methods known in the art.

Examples are given below of preferred uses of the enzyme and the antimicrobial agent of the invention.

Animal Feed

The term animal includes all animals, including human beings. Examples of animals are non-ruminants, and ruminants. Ruminant animals include, for example, animals such as sheep, goats, horses, and cattle, e.g. beef cattle, cows, and young calves. In a particular embodiment, the animal is a non-ruminant animal. Non-ruminant animals include monogastric animals, e.g. pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the enzyme and the antimicrobial agent can be fed to the animal before, after, or simultaneously with the diet. The latter is preferred.

In a particular embodiment, the enzyme and the antimicrobial agent, in the form in which they are added to the feed, or when being included in a feed additive, are well-defined. Well-defined means that the preparation is at least 50% pure as determined by Size-exclusion chromatography (see Example 12 of WO 01/58275). In other particular embodiments the preparation is at least 60, 70, 80, 85, 88, 90, 92, 94, or at least 95% pure as determined by this method.

A well-defined preparation is advantageous. For instance, it is much easier to dose correctly to the feed a preparation of enzyme and antimicrobial agent that is essentially free from interfering or contaminating other ingredients. The term dose correctly refers in particular to the objective of obtaining consistent and constant results, and the capability of optimising dosage based upon the desired effect.

For the use in animal feed, however, the enzyme and the antimicrobial agent need not be that pure; it may e.g. include additional enzymes and/or additional agents.

The preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original enzyme and antimicrobial agent preparation, whether used according to (a) or (b) above.

The animal feed usually comprises vegetable proteins, e.g. derived from legumes and cereals for example materials from plants of the families Fabaceae (Leguminosae), Cruciferaceae, Chenopodiaceae, and Poaceae, such as soy bean meal, lupin meal and rapeseed meal. The feed may also comprise an animal protein, such as meat and bone meal, and/or fish meal.

In a particular embodiment, the vegetable protein derives from one or more plants of the family Fabaceae, e.g. soybean, lupine, pea, or bean.

In another particular embodiment, the vegetable protein derives from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment, the enzyme and the antimicrobial agent improve the nutritional value of an animal feed, viz. e.g. the growth rate and/or the weight gain and/or the feed conversion (i.e. the weight of ingested feed relative to weight gain).

The enzyme and the antimicrobial agent can be added to the feed in any form, be it as a relatively pure product, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the enzyme and the antimicrobial agent of the invention, the animal feed additives of the invention contain at least one fat-soluble vitamin, and/or at least one water soluble vitamin, and/or at least one trace mineral, and/or optionally at least one macro mineral.

Further, optional, feed-additive ingredients are colouring agents, e.g. carotenoids such as beta-carotene, astaxanthin, and lutein; aroma compounds; stabilisers; polyunsaturated fatty acids; reactive oxygen generating species.

Usually fat- and water-soluble vitamins, as well as trace minerals form part of a so-called premix intended for addition to the feed, whereas macro minerals are usually separately added to the feed. Either of these composition types, when enriched with the enzyme and the antimicrobial agent of the invention, is an animal feed additive of the invention.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

An animal feed composition according to the invention has a crude protein content of 50-800 g/kg, and furthermore comprises at least one enzyme and antimicrobial agent of the invention.

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

In a particular embodiment, the animal feed composition of the invention contains at least one vegetable protein or protein source as defined above. It may also contain animal protein, such as Meat and Bone Meal, and/or Fish Meal, typically in an amount of 0-25%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can e.g. be manufactured as mash feed (non-pelleted) or pelleted feed. Typically, the milled feed-stuffs are mixed and sufficient amounts of essential vitamins and minerals are added according to the specifications for the species in question. The enzyme and the antimicrobial agent can be added as solid or liquid formulations. For example, a solid formulation is typically added before or during the mixing step; and a liquid preparation is typically added after the pelleting step. The enzyme and the antimicrobial agent may also be incorporated in a feed additive or premix.

These are particular embodiments of the invention:

A recombinant host cell comprising at least one nucleic acid construct that comprises i) a first nucleic acid sequence encoding a peptide, said peptide a) encompassing no more than 100 amino acids, and b) having antimicrobial activity; and ii) a second nucleic acid sequence encoding an enzyme; preferably the recombinant host cell comprises a first nucleic acid construct, and a second nucleic acid construct, wherein i) the first nucleic acid construct comprises the first nucleic acid sequence encoding the peptide; and ii) the second nucleic acid construct comprises the second nucleic acid sequence encoding the enzyme; more preferably the recombinant host cell comprises a nucleic acid construct comprising i) the first nucleic acid sequence encoding the peptide, and ii) the second nucleic acid sequence encoding the enzyme.

A nucleic acid construct comprising a first nucleic acid sequence encoding a peptide as defined above, and a second nucleic acid sequence encoding an enzyme as defined in claim 1, operably linked to one or more control sequences that direct the expression of the enzyme and the peptide in a suitable expression host.

A method for producing the enzyme and the peptide as defined above, the method comprising: (a) cultivating the recombinant host cell as described above to produce a supernatant comprising the enzyme and the peptide; and (b) recovering the enzyme and/or the peptide.

A fusion product comprising an enzyme, an antimicrobial peptide of no more than 100 amino acids, and a cleavable linker.

An animal feed additive comprising (a) at least one fusion product as defined above, (b) at least one fat soluble vitamin, and/or (c) at least one water soluble vitamin, and/or (d) at least one trace mineral.

An animal feed composition having a crude protein content of 50 to 800 g/kg and comprising at least one fusion product as defined above.

A transgenic plant, or plant part, capable of expressing the enzyme and the peptide as defined above.

A transgenic, non-human animal, or products, or elements thereof, capable of expressing the enzyme and the peptide as defined above.

Use of the fusion product as defined above in animal feed.

Use of co-expression of the peptide and the enzyme as defined above as a tool to improve the yield of the peptide and/or to improve overall production economy.

In the recombinant expression of an antimicrobial peptide encompassing no more than 100 amino acids, the use of a peptide protection domain, wherein at least 50% of the amino acid residues comprised in the peptide protection domain are D and/or E; wherein preferably the peptide protection domain encompasses between 1 and 100 amino acid residues.

A peptide, preferably isolated, wherein at least 50% of the amino acid residues are D (Asp) and/or E (Glu) and wherein the peptide has peptide protection activity, as well as the corresponding nucleic acid.

A method for identifying a protection peptide comprising at least one D (Asp) and/or E (Glu), the method comprising: a) providing a library of peptide protection candidates comprising at least one D and/or E; b) preparing a library of DNA constructs comprising a first DNA sequence encoding a member of the library of peptide protection candidate and a second DNA sequence encoding an antimicrobial peptide; c) transforming host cells with the library of DNA constructs of b) and cultivating the transformed host cells to obtain expression of the DNA constructs; d) estimating, and/or analyzing, viability of the transformed host cells, and/or estimating, and/or analyzing, the yield of antimicrobial peptide; and e) identifying peptide protection candidates which when used in a DNA construct according to step b), for transformation of a host cell according to step c), results in an increased viability of the host cell, and/or an increased yield of antimicrobial peptide, when estimated, and/or analyzed, according to step d); as well as a protection peptide obtainable, and/or obtained, by such method.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Generally, reference is made to Sambrook, Fritsch, and Maniatis, 1989, for the various standard protocols employed in the present experimental part.

Example 1

Assay for Antimicrobial Activity

This assay is particularly useful for assaying the antimicrobial activity of Novispirin and PR39. It is based on the protocol of Lehrer et al. (1991), J. Immunol. Methods 137: 167-173.

The selected target bacteria, e.g. *E. coli* ATCC 10536, or *B. subtilis* ATCC 6633 ($10^6$ colony forming units (CFU)) were added to 10 ml of underlay agarose (1% low electro-endosmosis agarose, 0.03% Trypticase soy broth, 10 mM sodium phosphate, pH 7.4, 37 degrees C.). The suspension was solidified in an INTEGRID Petri Dish (Becton Dickinson Labware, N.J.). A 3 mm Gel Puncher was used to punch holes in the underlay agarose (Amersham Pharmacia Biotech, Sweden). Samples expected to exhibit antimicrobial activity were added to the holes and incubated at 37 degrees C. for 3 hours. An overlay (LB media, 7.5% Agar) was poured on top and the plate was incubated overnight at 37 degrees C. Antimicrobial activity was seen as clearing zones around the wells. Living cells were counterstained by adding 10 ml, 0.2 mM MTT (3-(4,5-Dimethylthiazol-2-yl)-2,5-diphenyltetrazolium bromide; Thiazolyl blue).

Example 2

Use of Quenching Domains for the Expression of Antimicrobial Agents as Inclusion Bodies in *E. coli*

PR39 is a proline- and arginine-rich peptide which was originally isolated from pig intestine on the basis of antimicrobial activity (Agerberth, B. et al., Eur. J. Biochem. 202, 849-54 (1991)). The mature form of PR39 is composed of the following 39 amino acids:

(SEQ ID NO: 65)
RRRPRPPYLPRPRPPPFFPPRLPPRIPPGFPPRFPPRFP

Expression of antimicrobial peptides like e.g. PR39 in inclusion bodies has proven difficult for reasons that are not completely understood. In this experiment we evaluate the effect on the expression level of using various peptide protection domains of the invention.

The following fusion constructs were made in the pET31b+ expression vector system (commercially available from NOVAGEN):

```
PHM300:    KSI-NG-PR39

PHM370:    KSI-DP-PR39

PHM360:    KSI-DDDDDP(SEQ ID NO: 101)-PR39
           (SEQ ID NO: 65)

PHM350:    KSI-EEEEEDP(SEQ ID NO: 102)-PR39
           (SEQ ID NO: 65)
```

KSI is an insoluble fragment of Ketosteroid Isomerase that is known to promote the expression as insoluble inclusion bodies of the peptide or protein of interest. KSI forms part of the pET31b+ expression vector system.

PR39 designates the amino acid sequence of the mature PR39 peptide (SEQ ID NO: 65).

DP (Asp-Pro), DDDDDP (Asp-Asp-Asp-Asp-Asp-Pro) (SEQ ID NO: 101), and EEEEEDP (Glu-Glu-Glu-Glu-Glu-Asp-Pro) (SEQ ID NO: 102) are examples of peptide protection domains of the present invention.

NG (Asn-Gly) is an example of a linker which is not a protection domain of the invention.

Recombinant plasmids were transformed into *Escherichia coli* strain BL21-DE3 (forms part of the pET31b+ kit) and the expression of PR39 was evaluated through IPTG induction and SDS-PAGE. The results clearly showed increased expression from constructs PHM 370, 360 and 350 as compared to PHM300. Still further, the expression levels were clearly increased by construct PHM350 as compared to constructs PHM360 and PHM370, and by construct PHM360 as compared to construct PHM370.

After expression, the resulting fusion products can be cleaved by treatment with a weak acid (cleavage site: D-/-P), whereby the antimicrobial peptide regain its antimicrobial activity.

Example 3

Use of Quenching Domains in the Expression of Antimicrobial Agents in an *E. coli* Suicide Expression System This example makes use of the Suicide Expression System (SES) as described in WO 00/73433, see in particular Example 1.

The host cell used is *Escherichia coli* TOP10 which is commercially available from Invitrogen (araBADC$^-$, araEFGH$^+$).

Plasmids of series pHH (using plasmid pBAD/gIIIA) allow for the export of the antimicrobial peptides to the periplasmic space of *E. coli*, from where the peptides are allowed to interact with the cellular membranes. Plasmid pBAD/gIIIA is commercially available from Invitrogen. It is a pUC-derived expression vector designed for tightly regulated, recombinant protein expression in *E. coli*. This plasmid allows the cloning of peptides and proteins toxic to *E. coli*, as no expression of the recombinant peptides occurs in the absence of inducer in the growth medium. However, transcription and hence peptide synthesis, can be extensively induced. In series pHH, the gene III signal sequence in pBAD/gIIIA is located in front of the inducible promoter in order to mediate secretion of the peptide/protein in question. Gene III encodes pIII, one of the minor capsid proteins from the filamentous phage fd. pIII is synthesized with an 18 amino acid, N-terminal signal sequence, and requires the bacterial Sec system for insertion into the membrane. The signal sequence is removed after crossing the inner membrane, thus leaving the mature peptide. An NcoI restriction site immediately succeeds the signal sequence cleavage site.

The gene(s) encoding the antimicrobial peptide(s) are inserted in plasmids of the pHH series as NcoI-XbaI fragments. In case of PR39 this results in an introduction of amino acids MA at the N-terminus of the peptide (CCATGG). The natural codon usage is retained.

Five different N-terminal extensions to PR39 were constructed, viz.: E, DE, DDE, DDDE (SEQ ID NO: 103) and DDDDE (SEQ ID NO: 94).

These PR39-derivatives were made by PCR in a standard PCR reaction using a specific forward primer in connection with a general reverse primer pBAD-Rev, both of which are set out below. The PCR template was a pHH plasmid encoding the wildtype PR39 (wt PR39), SEQ ID NO: 65.

The PCR fragments were purified, restricted with NcoI and XbaI and cloned into the corresponding sites in pHH. The sequence of these constructs was verified by DNA sequencing using the primers pBAD-forw and pBAD-rev, see below.

The results from the testing in the SES system were that each of the five derivatives of PR39 resulted in a decreased inhibition as compared to the inhibition of wt PR-39. A decrease in inhibition is indicative of a decrease in antimicrobial activity and hence indicative of efficient quenching. Also, a gradually decreasing inhibition was observed along the following series of N-terminal extensions: E, DE, DDE, DDDE (SEQ ID NO: 103) and DDDDE (SEQ ID NO: 94). In other words, the largest inhibition was observed with E, followed by DE, then by DDE, then by DDDE (SEQ ID NO: 103), whereas DDDDE (SEQ ID NO: 94) exhibited the minimum inhibition observed in this experiment.

These are the primers that were used to amplify and sequence the five PR-39 derivatives:

```
pHH1531 (E-PR39)
Primer pHH1531-Forw:
                                    (SEQ ID NO: 66)
catagcaccatggaaaggagacgtccccgaccccatatttgcc pHH1532 (DE-PR39)
Primer pHH1532-Forw:
                                    (SEQ ID NO: 67)
catagcaccatggatgaaaggagacgtccccgaccccatatttgcc pHH1533 (DDE-PR39)
Primer pHH1533-Forw:
                                    (SEQ ID NO: 68)
catagcaccatggacgatgaaaggagacgtccccgaccccatatttgcc pHH1534 (DDDE-PR39)
Primer pHH1534-Forw:
                                    (SEQ ID NO: 69)
catagcaccatggatgacgatgaaaggagacgtccccgaccccatattt
gcc pHH1535 (DDDDE-PR39)
Primer pHH1535-Forw:
                                    (SEQ ID NO: 70)
catagcaccatggacgatgacgatgaaaggagacgtccccgaccccata
tttgcc pBAD-forw:
                                    (SEQ ID NO: 71)
CCATAAGATTAGCGGATCCTACC pBAD-rev:
                                    (SEQ ID NO: 72)
CTCTCATCCGCCAAAACAGCC
```

Example 4

Use of Quenching Domains in the Expression and Secretion of Antimicrobial Agents in Yeast This example illustrates the expression and secretion of two different antimicrobial peptides, Novispirin and PR39, in the yeast *Saccharomyces cerevisiae* using specific quenching domains.

Novispirin G10 is an antimicrobial peptide composed of the following amino acids:

```
KNLRRIIRKGIHIIKKYG.        (SEQ ID NO: 73)
```

First five different PR39 fusion constructs were made, viz. E-PR39, DE-PR39, DDE-PR39 DDDE(SEQ ID NO: 103)-PR39 and DDDDE(SEQ ID NO: 94)-PR39.

As some proteases specifically cleave after glutamic acid residues (E), the added quenching domain can be liberated from the AMP allowing for monitoring of the antimicrobial activity of the AMP.

The PR39-derivatives were amplified using specific Forward primers and a general reverse primer pBAD-rev that are indicated below in a standard PCR reaction. The PCR templates used were those generated in Example 3.

| Derivative | PCR Template | Fwdprimer | Revprimer |
|---|---|---|---|
| pHH3857 (E-PR39) | pHH1531 | pHH3857 fwd | pBAD rev |
| pHH3858 (DE-PR39) | pHH1532 | pHH3858 fwd | pBAD rev |
| pHH3859 (DDE-PR39) | pHH1533 | pHH3859 fwd | pBAD rev |
| pHH3860 (DDDE-PR39 | pHH1534 | pHH3860 fwd | pBAD rev |
| pHH3861 (DDDDE-PR39) | pHH1535 | pHH3861 fwd | pBAD rev |

Primer sequences
pHH3857 fwd:
(SEQ ID NO: 74)
AGGGGTATCGATGGCTAAGAGAGAAGCCGAAAGGAGACGTCCCCGACCCC
C pHH3858 fwd:
(SEQ ID NO: 75)
AGGGGTATCGATGGCTAAGAGAGAAGCCGATGAAAGGAGACGTCCCCGAC
CCCC pHH3859 fwd:
(SEQ ID NO: 76)
AGGGGTATCGATGGCTAAGAGAGAAGCCGACGATGAAAGGAGACGTCCCC
GACCCCC pHH3860 fwd:
(SEQ ID NO: 77)
AGGGGTATCGATGGCTAAGAGAGAAGCCGATGACGATGAAAGGAGACGTC
CCCGACCCCC pHH3861 fwd:
(SEQ ID NO: 78)
AGGGGTATCGATGGCTAAGAGAGAAGCCGACGATGACGATGAAAGGAGAC
GTCCCCGACCCC The resulting five PCR fragments were purified, restricted with ClaI and XbaI and cloned into a suitable yeast expression vector such as the commercially available vector pYES2. The five derivatives were verified by DNA sequencing, and transformed into a suitable strain of S. cerevisiae using a PEG/LiAc protocol.

Distinct bands with the expected molecular weight were observed in each of the five cultures indicating expression of the peptides. Again it appeared that the longer the quenching domains, the larger the amounts produced of the antimicrobial peptide, the effectiveness increasing in the order E<DE<DDE<DDDE<DDDDE. No bands were observed in supernatants of yeast cells harboring the control plasmid (without antimicrobial peptide).

The samples that encoded PR-39 showed distinct bands of the anticipated sizes on Tricine SDS-PAGE gels (Schagger & Von Jagow (87) Anal. Bioch. 166, 368-379.

Prior to digestion with the C-component protease no antimicrobial activity was detected in any supernatants that was analysed for antimicrobial activity as described in example 1. But after separation of the quenching domains from the antimicrobial peptide, clearing zones were observed in the samples encoding PR39. No clearing zone was detected in control samples.

In the same manner as described above, further constructs were made in yeast and found to allow for satisfactory expression and secretion of the antimicrobial peptide. The further constructs were the following:

```
pHH3864:  E-Novispirin (SEQ ID NO: 73)

pHH3865:  DDE-Novispirin (SEQ ID NO: 73)

pHH3866:  DDDDE(SEQ ID NO: 94)-Novispirin
          (SEQ ID NO: 73)

pHH3879:  DEDEDEDP(SEQ ID NO: 104)-Novispirin
          (SEQ ID NO: 73)

pHH3880:  DEDEDEDP(SEQ ID NO: 104)-PR-39
          (SEQ ID NO: 65)

pHH3883:  DDDGGEEEGGDDDP(SEQ ID NO: 105)-PR-39
          (SEQ ID NO: 65)

pHH3884:  DDDGGDDDPPDDDE(SEQ ID NO: 106)-PR-39
          (SEQ ID NO: 65).
```

Example 5

Exploiting the Distance Between the Quenching Domain and the Antimicrobial Agent To investigate the effect of the translational distance between the antimicrobial peptide and the quenching domain two new constructs were created. An expression setup similar to the one described in Example 4 was employed, i.e. a pYES2-derived vector utilizing the alpha-leader to allow secretion of the produced peptides.

In one construct, pHH3891, an eight amino acid glycine linker was inserted between PR-39 (SEQ ID NO: 65) and the quenching domain DDDDE (SEQ ID NO: 94). In the other construct, pHH3892, a twelve amino acid glycine linker was used. The plasmids were constructed by standard molecular biology methods, verified by DNA sequencing and transformed into yeast as described in Example 4.

```
pHH3891 (SEQ ID NO: 117):
DDDDE-GGGGGGGE-
RRRPRPPYLPRPRPPPFFPPRLPPRIPPGFPPRFPPRFP pHH3892 (SEQ ID NO: 118):
DDDDE-GGGGGGGGGGGE-
RRRPRPPYLPRPRPPPFFPPRLPPRIPPGFPPRFPPRFP
```

Two independent transformants of each of the two constructs were grown in the yeast minimal medium SC (see p. 174 in Methods in Yeast Genetics 2000 A Cold Spring Harbor Laboratory Course Manual by Dan Burke, ISBN 0-87969-588-9/0879695889) supplemented with 2% glucose and incubated under shaking at 35° C. for 3 days. The supernatants were harvested and analyzed on Bis-Tris gels as recommended by the manufacturer (Invitrogen, Carlsbad, Calif., USA).

All four supernatants contained a peptide with the apparent and expected size of 6 kDa. The peptides produced in pHH3891 and pHH3892 have a theoretical molecular weight (MW) of 6006 Da and 6234 Da, respectively.

The results indicate flexibility as regards the translational distance between the AMP and the quenching domain (protection peptide).

Example 6

Co-Expression of an Enzyme and an Antimicrobial Agent

This example illustrates co-expression in, and secretion from, recombinant bacteria of a pectate lyase enzyme and either of two antimicrobial peptides, as fusion proteins.

The gene encoding a pectate lyase derived from *Bacillus licheniformis* (amino acids 28-341 of SEQ ID NO: 2 of WO 00/75344) and a) an Anti Fungal Peptide (AFP) from *Aspergillus giganteus* (SEQ ID NO: 2 of WO 94/01459), or b) the antimicrobial peptide designated G10 novispirin (an artificial peptide having SEQ ID NO: 17 of U.S. Pat. No. 6,492, 328), was made and inserted along with the chloramphenicol resistance gene cat into the amyE locus on the chromosome of *Bacillus subtilis*. The *B. subtilis* host strain used was the protease deficient strain designated WB600asn (a chloramphenicol sensitive derivative of *B. subtilis* strain WB600 which is described in J. Bact. 1991. p. 4952-4958). Both of the fusion proteins according to a) and b) above were secreted into the culture broth.

The expression cassette was an amyQ promoter from *Bacillus amyloliquefaciens* in front of the cryIIIA promoter plus the mRNA stabilization element from *Bacillus thuringiensis*. (see U.S. Pat. No. 6,255,076, in particular the pDG268 neo system shown in FIG. 19 thereof).

The following DNA fragments were prepared:

(A) The Shine Delgarno sequence (SD) and the signal peptide were derived from the amyL gene of *Bacillus licheniformis* (ATCC 14580), viz. as the PCR fragment amplified by below primers 1 and 2 with Sac1 and Pst1 tails:

Primer 1:
tatagagctCCATTGAAAGGGGAGGAGAATC-3' (SEQ ID NO: 107)

Primer 2:
tataCTGCAGAATGAGGCAGCAAGAAGATGAGC-3'; (SEQ ID NO: 108)

(B) The coding region of the pectate lyase gene was also derived from *Bacillus licheniformis* (ATCC 14580), viz. as the PCR fragment amplified by below primers 3 and 4 with Pst1 and Nhe1 tails:

Primer 3:
tataCTGCAGCCGCGGCAGCTTCTGCCTTAAAC-3' (SEQ ID NO: 109)

Primer 4:
tataGCTAGCTGGATTGATTTTGCCGACTCCG-3'; (SEQ ID NO: 110)

(C1) A synthetic gene containing the coding region for the AFP sequence (nucleotides 1066-1218 of SEQ ID NO: 111) with Nhe1 and Mlu1 tails.

Primer 5:
tataacgcgTCTAGCAGTGGCACTTG-3' (SEQ ID NO: 113)

(C2) A synthetic gene containing the coding region for the G10 novispirin sequence (nucleotides 1236-1289 of SEQ ID NO: 114) with Nhe1 and Mlu1 tails.

Primer 6:
tataacgcgTTATCCGTATTTCTTAATG-3' (SEQ ID NO: 116)

The three fragments ((A)+(B)+(C1)), or ((A)+(B)+(C2)) were assembled after Restriction Enzyme digestion (Pst1+ Nhe1), DNA ligation and PCR amplification (PP1223-9 PCR primer 1+primer 5, DNA template: Ligation of fragment (A)+ (B)+(C1)), (PP1331-2 PCR primer 1+primer 6, DNA template: ligation of fragment (A)+(B)+(C2)), and finally inserted into the vector part of the pDG268neo plasmid as a Sac1 Mlu1 fragment (the unique Mlu1 site is situated in the C-terminal part of the Savinase gene in pDG268neo plasmid).

The plasmid with the above expression cassette and the cat gene flanked by amyE sequences was then transferred to competent cells of *Bacillus subtilis* WB600. Among the chloramphenicol resistant transformants a colony with the correct expression cassette inserted into the amyE gene was isolated, and the gene sequence of the inserted pectate lyase fusion peptide confirmed by DNA sequencing.

In the PP1223-9 *Bacillus subtilis* strain the pectate lyase gene is fused in frame to the DNA sequence encoding the AFP from *Aspergillus giganteus*. The fusion protein secreted from PP1223-9 (amino acids 1-368 of SEQ ID NO: 112) was identified as a major band of the correct size (40 kDal) by running the culture broth on an SDS PAGE gel:

(SEQ ID NO: 112)
MKQQKRLYARLLTLLFALIFLLPHSAAAAA*SALNSGKVNPLADFSLKGFA*

*ALNGGTTGGEGGQTVTVTTGDQLIAALKNKNANTPLKIYVNGTITTSNTS*

*ASKIDVKDVSNVSIVGSGTKGELKGIGIKIWRANNIIIRNLKIHEVASGD*

*KDAIGIEGPSKNIWVDHNELYHSLNVDKDYYDGLFDVKRDAEYITFSWNY*

*VHDGWKSMLMGSSDSDNYNRTITFHHNWFENLNSRVPSFRFGEGHIYNNY*

*FNKIIDSGINSRMGARIRIENNLFENAKDPIVSWYSSSPGYWHVSNNKFV*

*NSRGSMPTTSTTTYNPPYSYSLDNVDNVKSIVKQNAGVGKINPAS*<u>EATYP</u>

<u>GKCYKKDNICKYKAQSGKTGICKCYVKRCPRDGAKCDLDSYKGKCHC</u>.

The DNA fragment corresponding to SEQ ID NO: 112 is the PP1223-9 Sac1 Mlu1 DNA fragment of SEQ ID NO: 111.

The N-terminal signal peptide part of SEQ ID NO: 112 (underlined) is cleaved off before secretion of the mature fusion peptide. The underlined C-terminal tail region is the AFP. The mature pectate lyase part is shown in italics.

In the PP1331-2 *Bacillus subtilis* strain the pectate lyase gene is fused in frame to the DNA sequence encoding a larger linker (a stretch of negatively charged amino acids) and G10 novispirin. The fusion protein secreted from PP1331-2 (amino acids 1-392 of SEQ ID NO: 115) was identified as a major band of the correct size (43 kDal) by running the culture broth on an SDS PAGE gel:

MKQQKRLYARLLTLLFALIFLLPHSAAAAA*SALNSGKVNPLADFSLKGFAALNGGTTGG*    (SEQ ID NO: 115)

*EGGQTVTVTTGDQLIAALKNKNANTPLKIYVNGTITTSNTSASKIDVKDVSNVSIVGSGTKGELK*

*GIGIKIWRANNIIIRNLKIHEVASGDKDAIGIEGPSKNIWVDHNELYHSLNVDKDYYDGLFDVKRD*

*AEYITFSWNYVHDGWKSMLMGSSDSDNYNRTITFHHNWFENLNSRVSSFRFGEGHIYNNYF*

*NKIIDSGINSRMGARIRIENNLFENAKDPIVSWYSSSPGYWHVSNNKFVNSRGSMPTTSTTTY*

*NPPYSYSLDNVDNVKSIVKQNAGVGKINPASLDKREAEACEEERNAEEERRDEPDERDAQVE*

*HNAREAEADAEAVGPEAFADEDLDPWE*KNLRRIIRKGIHIIKKYG.

The N-terminal signal peptide part (underlined) of SEQ ID NO: 115 is cleaved off before secretion of the mature fusion peptide. The underlined C-terminal tail region is the G10 novispirin. The mature pectate lyase part is shown in italics. The DNA fragment corresponding to SEQ ID NO: 115 is the PP1331-2 Sac1 Mlu1 DNA fragment of SEQ ID NO: 114.

---

The invention claimed is:

1. A recombinant host cell comprising a first nucleic acid sequence encoding an antimicrobial peptide and a DNA sequence encoding a protection group, wherein (a) the antimicrobial peptide is cationic and has at least 10 amino acids and no more than 50 amino acids and (b) the protection group consists of between 1 and 50 amino acid residues and at least 50% of the amino acid residues are D (Asp) and/or E (Glu), wherein the protection group and the antimicrobial peptide are expressed as a fusion protein and wherein the protection group temporarily inactivates the antimicrobial peptide during its expression.

2. The recombinant host cell of claim 1, further comprising a second nucleic acid sequence encoding a heterologous enzyme.

3. The recombinant host cell of claim 2, wherein the first and/or the second nucleic acid sequence(s) is/are integrated into the chromosome of the host cell.

4. The recombinant host cell of claim 2, wherein the first nucleic acid sequence is incorporated in a first DNA construct and the second nucleic acid sequence is incorporated in a second DNA construct.

5. A method of producing an antimicrobial peptide and an enzyme, comprising:
   (a) cultivating the recombinant host cell of claim 2 under conditions conducive for producing the enzyme and a fusion protein comprising the protection group and the antimicrobial peptide; and
   (b) recovering the antimicrobial peptide and the enzyme.

6. A method of producing an antimicrobial peptide, comprising:
   (a) cultivating the recombinant host cell of claim 1 under conditions conducive for producing a fusion protein comprising the protection group and the antimicrobial peptide; and
   (b) recovering the antimicrobial peptide.

7. The method of claim 6, wherein the protection group consists of between 1 and 40 amino acid residues.

8. The method of claim 6, wherein the protection group consists of between 1 and 30 amino acid residues.

9. The method of claim 6, wherein the protection group consists of between 1 and 20 amino acid residues.

10. The method of claim 6, wherein the protection group consists of between 1 and 15 amino acid residues.

11. The method of claim 6, wherein the protection group consists of between 1 and 10 amino acid residues.

12. The method of claim 6, wherein at least 55% of the amino acid residues in the protection group are D (Asp) and/or E (Glu).

13. The method of claim 6, wherein at least 60% of the amino acid residues in the protection group are D (Asp) and/or E (Glu).

14. The method of claim 6, wherein at least 65% of the amino acid residues in the protection group are D (Asp) and/or E (Glu).

15. The method of claim 6, wherein at least 70% of the amino acid residues in the protection group are D (Asp) and/or E (Glu).

16. The method of claim 6, wherein at least 75% of the amino acid residues in the protection group are D (Asp) and/or E (Glu).

17. The method of claim 6, wherein at least 80% of the amino acid residues in the protection group are D (Asp) and/or E (Glu).

18. The method of claim 6, wherein at least 85% of the amino acid residues in the protection group are D (Asp) and/or E (Glu).

19. The method of claim 6, wherein at least 90% of the amino acid residues in the protection group are D (Asp) and/or E (Glu).

20. The method of claim 6, wherein at least 95% of the amino acid residues in the protection group are D (Asp) and/or E (Glu).

21. The method of claim 6, wherein the protection group consists of D (Asp) and/or E (Glu).

22. The method of claim 6, wherein the protection group does not contain any C (Cys) residues.

23. The method of claim 6, wherein the number of amino acid residues in the protection peptide is less than the number of amino acid residues in the antimicrobial peptide.

24. The method of claim 6, wherein the protection group is selected from the group consisting of D, DDDDDP (SEQ ID NO: 101), DDDDE (SEQ ID NO: 94), DDDE (SEQ ID NO: 103), DDDEE (SEQ ID NO: 93), DDDEEE (SEQ ID NO: 98), DDDGDDDPPDDDE (SEQ ID NO: 106), DDDG-GEEEGGDDDP (SEQ ID NO: 105), DDE, DDEED (SEQ ID NO: 96), DDEEE (SEQ ID NO: 92), DE, DED, DEDEDE (SEQ ID NO: 99), DEDEDEDP (SEQ ID NO: 104), DP, E, ED, EDE, EDEDE (SEQ ID NO: 97), EED, EEDDE (SEQ ID NO: 95), EEDDEE (SEQ ID NO: 100), and EEEEEDP (SEQ ID NO: 102).

25. The method of claim 6, further comprising cleaving the protection group from the antimicrobial peptide.

* * * * *